(12) United States Patent
Yoshino et al.

(10) Patent No.: US 9,932,557 B2
(45) Date of Patent: Apr. 3, 2018

(54) POLYPEPTIDE, SCAFFOLD COMPOSITION, COMPOSITION FOR CARTILAGE TISSUE RESTORATION, COMPOSITION FOR CARTILAGE CELL CULTURE, AND COMPOSITION FOR PROMOTING GLYCOSAMINOGLYCAN PRODUCTION

(71) Applicant: FUJIFILM Corporation, Tokyo (JP)

(72) Inventors: Yuichi Yoshino, Kanagawa (JP); Rie Iwata, Kanagawa (JP); Kentaro Nakamura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/640,218

(22) Filed: Mar. 6, 2015

(65) Prior Publication Data

US 2015/0175969 A1    Jun. 25, 2015

Related U.S. Application Data

(63) Continuation of application No. PCT/JP2013/075946, filed on Sep. 25, 2013.

(30) Foreign Application Priority Data

Sep. 26, 2012 (JP) ................................. 2012-213110

(51) Int. Cl.
| | | |
|---|---|---|
| C07K 14/00 | (2006.01) | |
| C07K 14/78 | (2006.01) | |
| A61K 51/08 | (2006.01) | |
| A61K 38/00 | (2006.01) | |
| C12N 5/077 | (2010.01) | |
| A61L 27/22 | (2006.01) | |

(52) U.S. Cl.
CPC ............ *C12N 5/0655* (2013.01); *A61K 38/00* (2013.01); *A61L 27/227* (2013.01); *C07K 14/78* (2013.01); *A61L 2300/252* (2013.01); *A61L 2430/06* (2013.01); *C12N 2501/998* (2013.01)

(58) Field of Classification Search
None
See application file for complete search history.

(56) References Cited

U.S. PATENT DOCUMENTS

| | | | | |
|---|---|---|---|---|
| 6,010,863 | A * | 1/2000 | Te Koppele ....... | G01N 33/6887 435/7.1 |
| 7,393,928 | B2 * | 7/2008 | Chang ................. | A23L 1/05625 435/320.1 |
| 2003/0095994 | A1 | 5/2003 | Geistlich et al. | |
| 2003/0219843 | A1 * | 11/2003 | Welsch .................. | G01N 33/68 435/7.92 |
| 2004/0077831 | A1 * | 4/2004 | Chapman .............. | A61K 35/18 530/350 |
| 2005/0058703 | A1 * | 3/2005 | Chang .................. | A61K 9/2077 424/456 |
| 2007/0031415 | A1 * | 2/2007 | Kinashi .................. | A61K 31/44 424/146.1 |

FOREIGN PATENT DOCUMENTS

| | | | |
|---|---|---|---|
| JP | 2003-180815 A | 7/2003 | |
| JP | 2007-528699 A | 10/2007 | |
| JP | 2008-537929 A | 10/2008 | |
| WO | 2002/100426 A1 | 12/2002 | |
| WO | 2004/085473 A2 | 10/2004 | |
| WO | 2006/091099 A2 | 8/2006 | |
| WO | WO 2008046543 A1 * | 4/2008 | ......... G01N 33/6893 |
| WO | 2008/133196 A1 | 11/2008 | |

OTHER PUBLICATIONS

SEQ Align 4 (2017) pp. 1-2.*
SEQ Align 36 (2017) pp. 1-2.*
SEQ Align 79 (2017) pp. 1-2.*
Chen et al. (2005) Type I and I1 collagen regulation of chondrogenic differentiation by mesenchymal progenitor cells, J. Orthopaedic Res., vol. 23, pp. 446-453.*
Notice of Reasons for Rejection, dated Sep. 29, 2015, issued in related JP Application No. 2014-538541, 6 pp. in English and Japanese.
Communication dated Mar. 22,2016, from the Japanese Patent Office in counterpart application No. 2014-538541.
Database GenBank [online], Accession No. CAA32030.1 <http://www.ncbi.nlm.nih.gov/protein/930050?report=genbank&log$=prottop&blast_rank=10&RID=5BWS64W1016>, Aug. 5, 1995, [retrieved on Dec. 2, 2013], DEFINITION: alpha-1 type 2 collagen (714 AA), partial [*Homo sapiens*].
Lee, C. R., et al., "Biosynthetic response of passaged chondrocytes in a type II collagen scaffold to mechanical compression", Journal of Biomedical Materials Research Part A, 2003, pp. 560-569, vol. 64A, No. 3.
Wu, Chun-Hsien, et al., "Effects of exogenous glycosaminoglycans on human chondrocytes cultivated on type II collagen scaffolds", Journal of Materials Science: Materials in Medicine, 2010, pp. 725-729, vol. 21, No. 2.
International Search Report of PCT/JP2013/075946 dated Dec. 10, 2013 [PCT/ISA/210], 6 pages.

(Continued)

*Primary Examiner* — Anand U Desai
*Assistant Examiner* — Samuel W Liu
(74) *Attorney, Agent, or Firm* — Sughrue Mion, PLLC

(57) ABSTRACT

A polypeptide having an amino acid sequence in which the number of RGD sequences contained per molecular weight of 10 kDa is not less than 0.30; the number of GFPGER sequences contained per molecular weight of 10 kDa is not less than 0.15; and the number of GVMGFP sequences contained per molecular weight of 10 kDa is less than 0.30; is provided. A scaffold composition, a composition for repairing a cartilage tissue, a composition for culturing cartilage cells, and a composition for promoting glycosaminoglycan production, which compositions contain the above polypeptide, are also provided.

12 Claims, 1 Drawing Sheet

(56) References Cited

OTHER PUBLICATIONS

Written Opinion of PCT/JP2013/075946 dated Dec. 10, 2013 [PCT/ISA/237], 8 pages.
Chiu, Li-Hsuan et al., "Differential effect of ECM molecules on re-expression of cartilaginous markers in near quiescent human chondrocytes," Journal of Cellular Physiology, 2011, vol. 226, No. 8, pp. 1981-1988, XP002754238, ISSN: 1097-4652.
Communication, dated Sep. 19, 2016, by the European Patent Office in counterpart European Patent Application No. 13842990.7.
Communication dated Nov. 3, 2016, from the State Intellectual Property Office of People's Republic of China in counterpart Application No. 201380048501.0.
Alpha-1 type 2 collagen (714 AA), partial [*Homosapiens*]; GenBank: CAA32030.1; Aug. 7, 1995; [online] ://www.ncbi.nlm.nih.gov/protein/CAA32030; (3 pages total).

\* cited by examiner

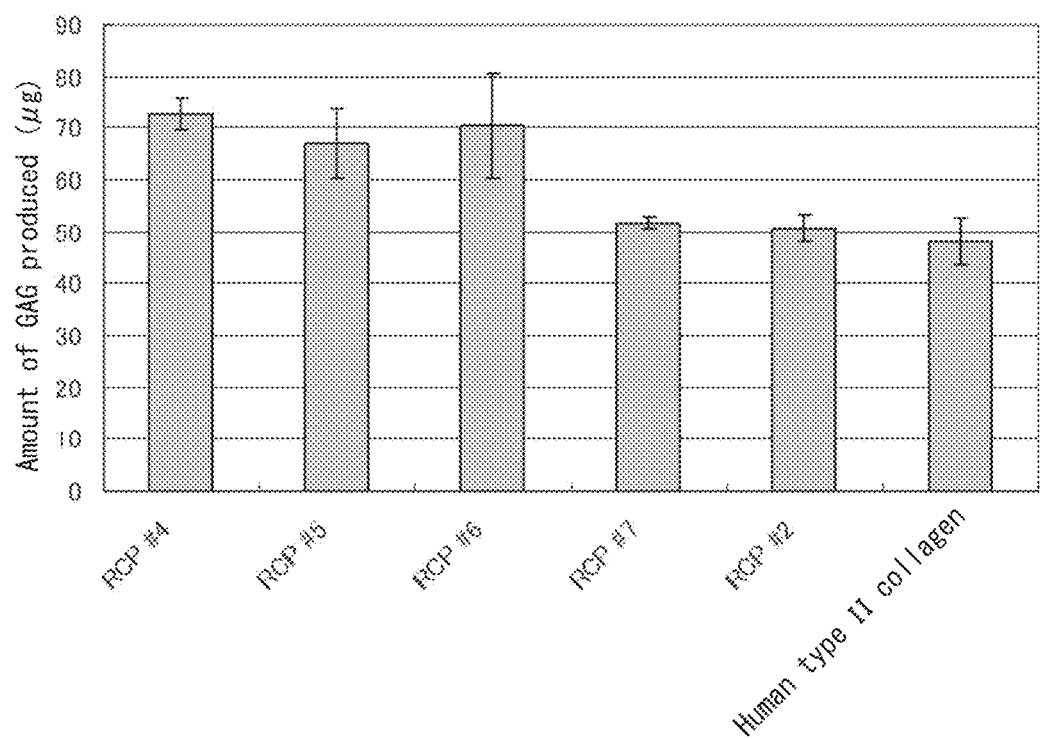

SEQUENCE LISTING

```
<160> NUMBER OF SEQ ID NOS: 21

<210> SEQ ID NO 1
<211> LENGTH: 506
<212> TYPE: PRT
<213> ORGANISM: Artificial Sequence
<220> FEATURE:
<223> OTHER INFORMATION: RCP#4

<400> SEQUENCE: 1

Gly Pro Gln Gly Ala Arg Gly Gln Pro Gly Val Met Gly Phe Pro Gly
1               5                   10                  15

Pro Lys Gly Ala Asn Gly Glu Pro Gly Lys Ala Gly Glu Lys Gly Leu
            20                  25                  30

Pro Gly Ala Pro Gly Leu Arg Gly Leu Pro Gly Lys Asp Gly Glu Ala
        35                  40                  45

Gly Ala Ala Gly Pro Pro Gly Pro Ala Gly Pro Ala Gly Glu Arg Gly
    50                  55                  60

Glu Gln Gly Ala Pro Gly Pro Gly Phe Gln Gly Leu Pro Gly Pro
65                  70                  75                  80

Pro Gly Pro Pro Gly Glu Gly Gly Lys Pro Gly Asp Gln Gly Val Pro
                85                  90                  95

Gly Glu Ala Gly Ala Pro Gly Leu Val Gly Pro Arg Gly Glu Arg Gly
            100                 105                 110
```

-continued

```
Phe Pro Gly Glu Arg Gly Ala Pro Gly Ala Gln Gly Leu Gln Gly Pro
    115                 120                 125
Arg Gly Leu Pro Gly Ala Pro Gly Pro Asp Gly Pro Lys Gly Ala Ala
130                 135                 140
Gly Pro Ala Gly Pro Pro Gly Ala Gln Gly Pro Pro Gly Leu Gln Gly
145                 150                 155                 160
Met Pro Gly Glu Arg Gly Ala Ala Gly Ile Ala Gly Pro Lys Gly Asp
                165                 170                 175
Arg Gly Asp Val Gly Glu Lys Gly Pro Glu Gly Ala Pro Gly Lys Asp
            180                 185                 190
Gly Gly Arg Gly Leu Gly Gly Pro Ile Gly Pro Pro Gly Pro Ala Gly
        195                 200                 205
Ala Asn Gly Glu Lys Gly Glu Val Gly Pro Pro Gly Pro Ala Gly Ala
    210                 215                 220
Ala Gly Ala Arg Gly Ala Pro Gly Glu Arg Gly Glu Ala Gly Pro Pro
225                 230                 235                 240
Gly Pro Ala Gly Phe Ala Gly Pro Pro Gly Ala Asp Gly Gln Pro Gly
                245                 250                 255
Ala Lys Gly Glu Gln Gly Glu Ala Gly Gln Lys Gly Asp Ala Gly Ala
            260                 265                 270
Pro Gly Pro Gln Gly Pro Gly Gly Ala Pro Gly Pro Gln Gly Pro Ala
        275                 280                 285
Gly Val Ala Gly Pro Lys Gly Ala Arg Gly Ala Gln Gly Pro Pro Gly
    290                 295                 300
Ala Ala Gly Phe Pro Gly Ala Ala Gly Arg Val Gly Pro Pro Gly Leu
305                 310                 315                 320
Gln Gly Asn Pro Gly Pro Pro Gly Pro Pro Gly Pro Ala Gly Lys Asp
                325                 330                 335
Gly Pro Lys Gly Ala Arg Gly Asp Ala Gly Pro Pro Gly Arg Ala Gly
            340                 345                 350
Glu Pro Gly Leu Gln Gly Pro Ala Gly Pro Pro Gly Glu Lys Gly Glu
        355                 360                 365
Pro Gly Asp Asp Gly Pro Pro Gly Ala Glu Gly Pro Pro Gly Pro Gln
    370                 375                 380
Gly Leu Ala Gly Gln Arg Gly Ile Val Gly Leu Pro Gly Gln Arg Gly
385                 390                 395                 400
Glu Arg Gly Phe Pro Gly Leu Pro Gly Pro Ala Gly Glu Pro Gly Lys
                405                 410                 415
Gln Gly Ala Pro Gly Ala Ala Gly Asp Arg Gly Pro Pro Gly Pro Val
            420                 425                 430
Gly Pro Pro Gly Leu Ala Gly Pro Ala Gly Glu Pro Gly Arg Glu Gly
        435                 440                 445
Gly Pro Gly Ala Asp Gly Pro Pro Gly Arg Asp Gly Ala Ala Gly Val
    450                 455                 460
Lys Gly Asp Arg Gly Glu Ala Gly Ala Val Gly Ala Pro Gly Ala Pro
465                 470                 475                 480
Gly Pro Pro Gly Ala Pro Gly Pro Ala Gly Pro Gly Pro Gln Gly
                485                 490                 495
Asp Arg Gly Glu Ala Gly Ala Gln Gly Pro
            500                 505

<210> SEQ ID NO 2
<211> LENGTH: 506
```

```
<212> TYPE: PRT
<213> ORGANISM: Artificial Sequence
<220> FEATURE:
<223> OTHER INFORMATION: RCP#5

<400> SEQUENCE: 2
```

| | | | | | | | | | | | | | | |
|---|---|---|---|---|---|---|---|---|---|---|---|---|---|---|
| Gly | Pro | Gln | Gly | Ala | Arg | Gly | Gln | Pro | Gly | Val | Met | Gly | Phe | Pro | Gly |
| 1 | | | | 5 | | | | | 10 | | | | | 15 | |
| Pro | Lys | Gly | Ala | Asn | Gly | Glu | Pro | Gly | Lys | Ala | Gly | Glu | Lys | Gly | Leu |
| | | | 20 | | | | | 25 | | | | | 30 | | |
| Pro | Gly | Ala | Pro | Gly | Leu | Arg | Gly | Leu | Pro | Gly | Lys | Asp | Gly | Glu | Ala |
| | | | 35 | | | | | 40 | | | | | 45 | | |
| Gly | Ala | Ala | Gly | Pro | Pro | Gly | Pro | Ala | Gly | Pro | Ala | Gly | Glu | Arg | Gly |
| | 50 | | | | | 55 | | | | | 60 | | | | |
| Glu | Gln | Gly | Ala | Pro | Gly | Pro | Gly | Phe | Gln | Gly | Leu | Pro | Gly | Pro |
| 65 | | | | | 70 | | | | | 75 | | | | | 80 |
| Pro | Gly | Pro | Pro | Gly | Glu | Gly | Lys | Pro | Gly | Asp | Gln | Gly | Val | Pro |
| | | | | 85 | | | | | 90 | | | | | 95 | |
| Gly | Glu | Ala | Gly | Ala | Pro | Gly | Leu | Val | Gly | Pro | Arg | Gly | Glu | Arg | Gly |
| | | | | 100 | | | | | 105 | | | | | 110 | |
| Phe | Pro | Gly | Glu | Arg | Gly | Lys | Pro | Gly | Ala | Gln | Gly | Leu | Gln | Gly | Pro |
| | | | 115 | | | | | 120 | | | | | 125 | | |
| Arg | Gly | Leu | Pro | Gly | Ala | Pro | Gly | Lys | Asp | Gly | Pro | Lys | Gly | Ala | Ala |
| | 130 | | | | | 135 | | | | | 140 | | | | |
| Gly | Pro | Ala | Gly | Pro | Pro | Gly | Ala | Gln | Gly | Pro | Pro | Gly | Leu | Gln | Gly |
| 145 | | | | | 150 | | | | | 155 | | | | | 160 |
| Met | Pro | Gly | Glu | Arg | Gly | Ala | Ala | Gly | Ile | Ala | Gly | Pro | Lys | Gly | Asp |
| | | | | 165 | | | | | 170 | | | | | 175 | |
| Arg | Gly | Asp | Val | Gly | Glu | Lys | Gly | Pro | Glu | Gly | Ala | Pro | Gly | Lys | Asp |
| | | | 180 | | | | | 185 | | | | | 190 | | |
| Gly | Gly | Arg | Gly | Leu | Gly | Gly | Pro | Ile | Gly | Pro | Pro | Gly | Pro | Ala | Gly |
| | | | 195 | | | | | 200 | | | | | 205 | | |
| Ala | Asn | Gly | Glu | Lys | Gly | Glu | Val | Gly | Pro | Pro | Gly | Pro | Ala | Gly | Ala |
| | 210 | | | | | 215 | | | | | 220 | | | | |
| Ala | Gly | Ala | Arg | Gly | Ala | Pro | Gly | Glu | Arg | Gly | Glu | Lys | Gly | Pro | Pro |
| 225 | | | | | 230 | | | | | 235 | | | | | 240 |
| Gly | Pro | Ala | Gly | Phe | Ala | Gly | Pro | Pro | Gly | Ala | Asp | Gly | Gln | Pro | Gly |
| | | | | 245 | | | | | 250 | | | | | 255 | |
| Ala | Lys | Gly | Glu | Gln | Gly | Glu | Ala | Gly | Gln | Lys | Gly | Asp | Ala | Gly | Ala |
| | | | 260 | | | | | 265 | | | | | 270 | | |
| Pro | Gly | Pro | Gln | Gly | Pro | Lys | Gly | Ala | Pro | Gly | Pro | Gln | Gly | Pro | Ala |
| | | | 275 | | | | | 280 | | | | | 285 | | |
| Gly | Val | Ala | Gly | Pro | Lys | Gly | Ala | Arg | Gly | Ala | Gln | Gly | Pro | Pro | Gly |
| | 290 | | | | | 295 | | | | | 300 | | | | |
| Ala | Ala | Gly | Phe | Pro | Gly | Ala | Ala | Gly | Arg | Val | Gly | Pro | Pro | Gly | Leu |
| 305 | | | | | 310 | | | | | 315 | | | | | 320 |
| Gln | Gly | Asn | Pro | Gly | Pro | Pro | Gly | Pro | Pro | Gly | Pro | Ala | Gly | Lys | Asp |
| | | | | 325 | | | | | 330 | | | | | 335 | |
| Gly | Pro | Lys | Gly | Ala | Arg | Gly | Asp | Ala | Gly | Pro | Pro | Gly | Arg | Ala | Gly |
| | | | 340 | | | | | 345 | | | | | 350 | | |
| Glu | Pro | Gly | Leu | Gln | Gly | Pro | Ala | Gly | Pro | Pro | Gly | Glu | Lys | Gly | Glu |
| | | | 355 | | | | | 360 | | | | | 365 | | |
| Pro | Gly | Asp | Asp | Gly | Pro | Pro | Gly | Ala | Glu | Gly | Pro | Pro | Gly | Pro | Gln |
| | | | 370 | | | | | 375 | | | | | 380 | | |

```
Gly Leu Ala Gly Gln Arg Gly Ile Val Gly Leu Pro Gly Gln Arg Gly
385                 390                 395                 400

Glu Arg Gly Phe Pro Gly Leu Pro Gly Pro Lys Gly Glu Pro Gly Lys
            405                 410                 415

Gln Gly Ala Pro Gly Ala Lys Gly Asp Arg Gly Pro Pro Gly Pro Val
            420                 425                 430

Gly Pro Pro Gly Leu Ala Gly Pro Ala Gly Glu Pro Gly Arg Glu Gly
            435                 440                 445

Gly Pro Gly Ala Asp Gly Pro Pro Gly Arg Asp Gly Ala Ala Gly Val
            450                 455                 460

Lys Gly Asp Arg Gly Glu Lys Gly Ala Val Gly Ala Pro Gly Ala Pro
465                 470                 475                 480

Gly Pro Pro Gly Ala Pro Gly Pro Ala Gly Pro Pro Gly Pro Gln Gly
            485                 490                 495

Asp Arg Gly Glu Ala Gly Ala Gln Gly Pro
            500                 505

<210> SEQ ID NO 3
<211> LENGTH: 644
<212> TYPE: PRT
<213> ORGANISM: Artificial Sequence
<220> FEATURE:
<223> OTHER INFORMATION: RCP#6

<400> SEQUENCE: 3

Met Gly Phe Pro Gly Pro Lys Gly Ala Asn Gly Glu Pro Gly Lys Ala
1               5                   10                  15

Gly Glu Lys Gly Leu Pro Gly Ala Pro Gly Leu Arg Gly Leu Pro Gly
            20                  25                  30

Lys Asp Gly Glu Ala Gly Ala Ala Gly Pro Pro Gly Pro Ala Gly Pro
            35                  40                  45

Ala Gly Glu Arg Gly Glu Gln Gly Ala Pro Gly Pro Pro Gly Phe Gln
            50                  55                  60

Gly Leu Pro Gly Pro Pro Gly Pro Pro Gly Glu Gly Gly Lys Pro Gly
65                  70                  75                  80

Asp Gln Gly Val Pro Gly Glu Ala Gly Ala Pro Gly Leu Val Gly Pro
            85                  90                  95

Arg Gly Glu Arg Gly Phe Pro Gly Glu Arg Gly Lys Pro Gly Ala Gln
            100                 105                 110

Gly Leu Gln Gly Pro Arg Gly Leu Pro Gly Ala Pro Gly Lys Asp Gly
            115                 120                 125

Pro Lys Gly Ala Ala Gly Pro Ala Gly Pro Pro Gly Ala Gln Gly Pro
            130                 135                 140

Pro Gly Leu Gln Gly Met Pro Gly Glu Arg Gly Ala Ala Gly Ile Ala
145                 150                 155                 160

Gly Pro Lys Gly Asp Arg Gly Asp Val Gly Glu Lys Gly Pro Glu Gly
            165                 170                 175

Ala Pro Gly Lys Asp Gly Gly Arg Gly Leu Gly Gly Pro Ile Gly Pro
            180                 185                 190

Pro Gly Pro Ala Gly Ala Asn Gly Glu Lys Gly Glu Val Gly Pro Pro
            195                 200                 205

Gly Pro Ala Gly Ala Ala Gly Ala Arg Gly Ala Pro Gly Glu Arg Gly
            210                 215                 220

Glu Lys Gly Pro Pro Gly Pro Ala Gly Phe Ala Gly Pro Pro Gly Ala
225                 230                 235                 240
```

Asp Gly Gln Pro Gly Ala Lys Gly Glu Gln Gly Glu Ala Gly Gln Lys
            245                 250                 255

Gly Asp Ala Gly Ala Pro Gly Pro Gln Gly Pro Lys Gly Ala Pro Gly
        260                 265                 270

Pro Gln Gly Pro Ala Gly Val Ala Gly Pro Lys Gly Ala Arg Gly Ala
        275                 280                 285

Gln Gly Pro Pro Gly Ala Ala Gly Phe Pro Gly Ala Ala Gly Arg Val
        290                 295                 300

Gly Pro Pro Gly Leu Gln Gly Asn Pro Gly Pro Gly Pro Pro Gly
305                 310                 315                 320

Pro Ala Gly Lys Asp Gly Pro Lys Gly Ala Arg Gly Asp Ala Gly Pro
        325                 330                 335

Pro Gly Arg Ala Gly Glu Pro Gly Leu Gln Gly Pro Ala Gly Pro Pro
        340                 345                 350

Gly Glu Lys Gly Glu Pro Gly Asp Asp Gly Pro Pro Gly Ala Glu Gly
        355                 360                 365

Pro Pro Gly Pro Gln Gly Leu Ala Gly Gln Arg Gly Ile Val Gly Leu
        370                 375                 380

Pro Gly Gln Arg Gly Glu Arg Gly Phe Pro Gly Leu Pro Gly Pro Lys
385                 390                 395                 400

Gly Glu Pro Gly Lys Gln Gly Ala Pro Gly Ala Lys Gly Asp Arg Gly
        405                 410                 415

Pro Pro Gly Pro Val Gly Pro Pro Gly Leu Ala Gly Pro Ala Gly Glu
        420                 425                 430

Pro Gly Arg Glu Gly Gly Pro Gly Ala Asp Gly Pro Pro Gly Arg Asp
        435                 440                 445

Gly Ala Ala Gly Val Lys Gly Asp Arg Gly Glu Lys Gly Ala Val Gly
        450                 455                 460

Ala Pro Gly Ala Pro Gly Pro Pro Gly Ala Pro Gly Pro Ala Gly Pro
465                 470                 475                 480

Pro Gly Pro Gln Gly Asp Arg Gly Glu Ala Gly Ala Gln Gly Pro Met
        485                 490                 495

Gly Phe Pro Gly Pro Lys Gly Ala Asn Gly Glu Pro Gly Lys Ala Gly
        500                 505                 510

Glu Lys Gly Leu Pro Gly Ala Pro Gly Leu Arg Gly Leu Pro Gly Lys
        515                 520                 525

Asp Gly Glu Ala Gly Ala Gln Gly Pro Pro Gly Pro Ala Gly Pro Ala
        530                 535                 540

Gly Glu Arg Gly Glu Gln Gly Ala Pro Gly Pro Pro Gly Phe Gln Gly
545                 550                 555                 560

Leu Pro Gly Pro Pro Gly Pro Pro Gly Glu Gly Gly Lys Pro Gly Asp
            565                 570                 575

Gln Gly Val Pro Gly Glu Ala Gly Ala Pro Gly Leu Val Gly Pro Arg
        580                 585                 590

Gly Glu Arg Gly Phe Pro Gly Glu Arg Gly Lys Pro Gly Ala Gln Gly
        595                 600                 605

Leu Gln Gly Pro Arg Gly Leu Pro Gly Ala Pro Gly Lys Asp Gly Pro
        610                 615                 620

Lys Gly Ala Ala Gly Ala Gly Pro Pro Gly Ala Gln Gly Pro Pro
625                 630                 635                 640

Gly Leu Gln Gly

<210> SEQ ID NO 4

<211> LENGTH: 1487
<212> TYPE: PRT
<213> ORGANISM: Homo sapiens

<400> SEQUENCE: 4

```
Met Ile Arg Leu Gly Ala Pro Gln Thr Leu Val Leu Leu Thr Leu Leu
1               5                   10                  15

Val Ala Ala Val Leu Arg Cys Gln Gly Gln Asp Val Gln Glu Ala Gly
            20                  25                  30

Ser Cys Val Gln Asp Gly Gln Arg Tyr Asn Asp Lys Asp Val Trp Lys
        35                  40                  45

Pro Glu Pro Cys Arg Ile Cys Val Cys Asp Thr Gly Thr Val Leu Cys
    50                  55                  60

Asp Asp Ile Ile Cys Glu Asp Val Lys Asp Cys Leu Ser Pro Glu Ile
65                  70                  75                  80

Pro Phe Gly Glu Cys Cys Pro Ile Cys Pro Thr Asp Leu Ala Thr Ala
                85                  90                  95

Ser Gly Gln Pro Gly Pro Lys Gly Gln Lys Gly Glu Pro Gly Asp Ile
            100                 105                 110

Lys Asp Ile Val Gly Pro Lys Gly Pro Pro Gly Pro Gln Gly Pro Ala
        115                 120                 125

Gly Glu Gln Gly Pro Arg Gly Asp Arg Gly Asp Lys Gly Glu Lys Gly
    130                 135                 140

Ala Pro Gly Pro Arg Gly Arg Asp Gly Glu Pro Gly Thr Pro Gly Asn
145                 150                 155                 160

Pro Gly Pro Pro Gly Pro Pro Gly Pro Pro Gly Pro Pro Gly Leu Gly
                165                 170                 175

Gly Asn Phe Ala Ala Gln Met Ala Gly Gly Phe Asp Glu Lys Ala Gly
            180                 185                 190

Gly Ala Gln Leu Gly Val Met Gln Gly Pro Met Gly Pro Met Gly Pro
        195                 200                 205

Arg Gly Pro Pro Gly Pro Ala Gly Ala Pro Gly Pro Gln Gly Phe Gln
    210                 215                 220

Gly Asn Pro Gly Glu Pro Gly Glu Pro Gly Val Ser Gly Pro Met Gly
225                 230                 235                 240

Pro Arg Gly Pro Pro Gly Pro Pro Gly Lys Pro Gly Asp Asp Gly Glu
                245                 250                 255

Ala Gly Lys Pro Gly Lys Ala Gly Glu Arg Gly Pro Pro Gly Pro Gln
            260                 265                 270

Gly Ala Arg Gly Phe Pro Gly Thr Pro Gly Leu Pro Gly Val Lys Gly
        275                 280                 285

His Arg Gly Tyr Pro Gly Leu Asp Gly Ala Lys Gly Glu Ala Gly Ala
    290                 295                 300

Pro Gly Val Lys Gly Glu Ser Gly Ser Pro Gly Glu Asn Gly Ser Pro
305                 310                 315                 320

Gly Pro Met Gly Pro Arg Gly Leu Pro Gly Glu Arg Gly Arg Thr Gly
                325                 330                 335

Pro Ala Gly Ala Ala Gly Ala Arg Gly Asn Asp Gly Gln Pro Gly Pro
            340                 345                 350

Ala Gly Pro Pro Gly Pro Val Gly Pro Ala Gly Gly Pro Gly Phe Pro
        355                 360                 365

Gly Ala Pro Gly Ala Lys Gly Glu Ala Gly Pro Thr Gly Ala Arg Gly
    370                 375                 380

Pro Glu Gly Ala Gln Gly Pro Arg Gly Glu Pro Gly Thr Pro Gly Ser
```

-continued

```
             385                 390                 395                 400
Pro Gly Pro Ala Gly Ala Ser Gly Asn Pro Gly Thr Asp Gly Ile Pro
                    405                 410                 415
Gly Ala Lys Gly Ser Ala Gly Ala Pro Gly Ile Ala Gly Ala Pro Gly
                420                 425                 430
Phe Pro Gly Pro Arg Gly Pro Pro Gly Pro Gln Gly Ala Thr Gly Pro
            435                 440                 445
Leu Gly Pro Lys Gly Gln Thr Gly Glu Pro Gly Ile Ala Gly Phe Lys
        450                 455                 460
Gly Glu Gln Gly Pro Lys Gly Glu Pro Gly Pro Ala Gly Pro Gln Gly
465                 470                 475                 480
Ala Pro Gly Pro Ala Gly Glu Glu Gly Lys Arg Gly Ala Arg Gly Glu
                    485                 490                 495
Pro Gly Gly Val Gly Pro Ile Gly Pro Pro Gly Glu Arg Gly Ala Pro
                500                 505                 510
Gly Asn Arg Gly Phe Pro Gly Gln Asp Gly Leu Ala Gly Pro Lys Gly
            515                 520                 525
Ala Pro Gly Glu Arg Gly Pro Ser Gly Leu Ala Gly Pro Lys Gly Ala
        530                 535                 540
Asn Gly Asp Pro Gly Arg Pro Gly Glu Pro Gly Leu Pro Gly Ala Arg
545                 550                 555                 560
Gly Leu Thr Gly Arg Pro Gly Asp Ala Gly Pro Gln Gly Lys Val Gly
                    565                 570                 575
Pro Ser Gly Ala Pro Gly Glu Asp Gly Arg Pro Gly Pro Pro Gly Pro
                580                 585                 590
Gln Gly Ala Arg Gly Gln Pro Gly Val Met Gly Phe Pro Gly Pro Lys
            595                 600                 605
Gly Ala Asn Gly Glu Pro Gly Lys Ala Gly Glu Lys Gly Leu Pro Gly
        610                 615                 620
Ala Pro Gly Leu Arg Gly Leu Pro Gly Lys Asp Gly Glu Thr Gly Ala
625                 630                 635                 640
Ala Gly Pro Pro Gly Pro Ala Gly Pro Ala Gly Glu Arg Gly Glu Gln
                    645                 650                 655
Gly Ala Pro Gly Pro Ser Gly Phe Gln Gly Leu Pro Gly Pro Pro Gly
                660                 665                 670
Pro Pro Gly Glu Gly Gly Lys Pro Gly Asp Gln Gly Val Pro Gly Glu
            675                 680                 685
Ala Gly Ala Pro Gly Leu Val Gly Pro Arg Gly Glu Arg Gly Phe Pro
        690                 695                 700
Gly Glu Arg Gly Ser Pro Gly Ala Gln Gly Leu Gln Gly Pro Arg Gly
705                 710                 715                 720
Leu Pro Gly Thr Pro Gly Thr Asp Gly Pro Lys Gly Ala Ser Gly Pro
                    725                 730                 735
Ala Gly Pro Pro Gly Ala Gln Gly Pro Pro Gly Leu Gln Gly Met Pro
                740                 745                 750
Gly Glu Arg Gly Ala Ala Gly Ile Ala Gly Pro Lys Gly Asp Arg Gly
            755                 760                 765
Asp Val Gly Glu Lys Gly Pro Glu Gly Ala Pro Gly Lys Asp Gly Gly
        770                 775                 780
Arg Gly Leu Thr Gly Pro Ile Gly Pro Pro Gly Pro Ala Gly Ala Asn
785                 790                 795                 800
Gly Glu Lys Gly Glu Val Gly Pro Pro Gly Pro Ala Gly Ser Ala Gly
                    805                 810                 815
```

-continued

Ala Arg Gly Ala Pro Gly Glu Arg Gly Glu Thr Gly Pro Pro Gly Pro
            820                 825                 830

Ala Gly Phe Ala Gly Pro Pro Gly Ala Asp Gly Gln Pro Gly Ala Lys
            835                 840                 845

Gly Glu Gln Gly Glu Ala Gly Gln Lys Gly Asp Ala Gly Ala Pro Gly
            850                 855                 860

Pro Gln Gly Pro Ser Gly Ala Pro Gly Pro Gln Gly Pro Thr Gly Val
865                 870                 875                 880

Thr Gly Pro Lys Gly Ala Arg Gly Ala Gln Gly Pro Pro Gly Ala Thr
                885                 890                 895

Gly Phe Pro Gly Ala Ala Gly Arg Val Gly Pro Pro Gly Ser Asn Gly
            900                 905                 910

Asn Pro Gly Pro Pro Gly Pro Pro Gly Pro Ser Gly Lys Asp Gly Pro
            915                 920                 925

Lys Gly Ala Arg Gly Asp Ser Gly Pro Pro Gly Arg Ala Gly Glu Pro
930                 935                 940

Gly Leu Gln Gly Pro Ala Gly Pro Pro Gly Glu Lys Gly Glu Pro Gly
945                 950                 955                 960

Asp Asp Gly Pro Ser Gly Ala Glu Gly Pro Pro Gly Pro Gln Gly Leu
                965                 970                 975

Ala Gly Gln Arg Gly Ile Val Gly Leu Pro Gly Gln Arg Gly Glu Arg
            980                 985                 990

Gly Phe Pro Gly Leu Pro Gly Pro Ser Gly Glu Pro Gly Lys Gln Gly
            995                 1000                 1005

Ala Pro Gly Ala Ser Gly Asp Arg Gly Pro Pro Gly Pro Val Gly
    1010                 1015                 1020

Pro Pro Gly Leu Thr Gly Pro Ala Gly Glu Pro Gly Arg Glu Gly
    1025                 1030                 1035

Ser Pro Gly Ala Asp Gly Pro Pro Gly Arg Asp Gly Ala Ala Gly
    1040                 1045                 1050

Val Lys Gly Asp Arg Gly Glu Thr Gly Ala Val Gly Ala Pro Gly
    1055                 1060                 1065

Ala Pro Gly Pro Pro Gly Ser Pro Gly Pro Ala Gly Pro Thr Gly
    1070                 1075                 1080

Lys Gln Gly Asp Arg Gly Glu Ala Gly Ala Gln Gly Pro Met Gly
    1085                 1090                 1095

Pro Ser Gly Pro Ala Gly Ala Arg Gly Ile Gln Gly Pro Gln Gly
    1100                 1105                 1110

Pro Arg Gly Asp Lys Gly Glu Ala Gly Glu Pro Gly Glu Arg Gly
    1115                 1120                 1125

Leu Lys Gly His Arg Gly Phe Thr Gly Leu Gln Gly Leu Pro Gly
    1130                 1135                 1140

Pro Pro Gly Pro Ser Gly Asp Gln Gly Ala Ser Gly Pro Ala Gly
    1145                 1150                 1155

Pro Ser Gly Pro Arg Gly Pro Pro Gly Pro Val Gly Pro Ser Gly
    1160                 1165                 1170

Lys Asp Gly Ala Asn Gly Ile Pro Gly Pro Ile Gly Pro Pro Gly
    1175                 1180                 1185

Pro Arg Gly Arg Ser Gly Glu Thr Gly Pro Ala Gly Pro Pro Gly
    1190                 1195                 1200

Asn Pro Gly Pro Pro Gly Pro Pro Gly Pro Pro Gly Pro Gly Ile
    1205                 1210                 1215

```
Asp Met Ser Ala Phe Ala Gly Leu Gly Pro Arg Glu Lys Gly Pro
    1220            1225                1230
Asp Pro Leu Gln Tyr Met Arg Ala Asp Gln Ala Ala Gly Gly Leu
    1235            1240                1245
Arg Gln His Asp Ala Glu Val Asp Ala Thr Leu Lys Ser Leu Asn
    1250            1255                1260
Asn Gln Ile Glu Ser Ile Arg Ser Pro Glu Gly Ser Arg Lys Asn
    1265            1270                1275
Pro Ala Arg Thr Cys Arg Asp Leu Lys Leu Cys His Pro Glu Trp
    1280            1285                1290
Lys Ser Gly Asp Tyr Trp Ile Asp Pro Asn Gln Gly Cys Thr Leu
    1295            1300                1305
Asp Ala Met Lys Val Phe Cys Asn Met Glu Thr Gly Glu Thr Cys
    1310            1315                1320
Val Tyr Pro Asn Pro Ala Asn Val Pro Lys Lys Asn Trp Trp Ser
    1325            1330                1335
Ser Lys Ser Lys Glu Lys Lys His Ile Trp Phe Gly Glu Thr Ile
    1340            1345                1350
Asn Gly Gly Phe His Phe Ser Tyr Gly Asp Asp Asn Leu Ala Pro
    1355            1360                1365
Asn Thr Ala Asn Val Gln Met Thr Phe Leu Arg Leu Leu Ser Thr
    1370            1375                1380
Glu Gly Ser Gln Asn Ile Thr Tyr His Cys Lys Asn Ser Ile Ala
    1385            1390                1395
Tyr Leu Asp Glu Ala Ala Gly Asn Leu Lys Lys Ala Leu Leu Ile
    1400            1405                1410
Gln Gly Ser Asn Asp Val Glu Ile Arg Ala Glu Gly Asn Ser Arg
    1415            1420                1425
Phe Thr Tyr Thr Ala Leu Lys Asp Gly Cys Thr Lys His Thr Gly
    1430            1435                1440
Lys Trp Gly Lys Thr Val Ile Glu Tyr Arg Ser Gln Lys Thr Ser
    1445            1450                1455
Arg Leu Pro Ile Ile Asp Ile Ala Pro Met Asp Ile Gly Gly Pro
    1460            1465                1470
Glu Gln Glu Phe Gly Val Asp Ile Gly Pro Val Cys Phe Leu
    1475            1480                1485

<210> SEQ ID NO 5
<211> LENGTH: 1553
<212> TYPE: DNA
<213> ORGANISM: Artificial Sequence
<220> FEATURE:
<223> OTHER INFORMATION: polynucleotide #4

<400> SEQUENCE: 5
ctcgagaaaa gagaggctga agctggtccc caaggtgcaa gaggccaacc aggtgtaatg      60
ggttttcctg gtcccaaagg agccaatggt gaacccggaa aggctggcga aaaggactg     120 cctggtgctc caggattgag agggcttcca ggtaaagacg gtgaggctgg tgccgcagga     180
ccaccaggtc ccgccggccc tgctggagaa agaggcgaac aaggcgctcc gggcccaccc     240
ggtttccagg ggctgccagg acctcctggc ccaccagggg aaggagggaa gccaggtgac     300
caaggtgttc caggggaagc tggtgcccct ggcttagtcg gtccaagagg agaaaggggc     360
tttcctggag agcgaggagc accaggagcc cagggtttgc agggcccaag aggttttgcct    420 ggagctcccg gaccagacgg tccaaagggt gctgccggtc ctgctggtcc accgggtgca     480
```

```
caaggacctc caggccttca gggcatgcct ggtgagagag gtgccgctgg aatagccgga      540
cccaagggcg atagagggga tgttggcgaa aagggtcctg aaggagctcc cggcaaagat      600
ggtggacgtg gtctaggcgg acctattggg cctccaggac ccgccggagc taacggtgag      660
aaaggcgaag taggaccacc tggaccggcc ggtgctgctg gtgctcgtgg tgcacccgga      720
gagagaggtg aagctggtcc accgggtcca gctggctttg ctggtccgcc cggagcagat      780
ggacaaccag gagccaaggg tgaacaagga gaagcaggcc aaaagggtga tgctggtgca      840
ccaggacccc aaggtcctgg aggtgctcca ggtcctcagg acctgcaggt gttgcaggc      900 cctaaaggag cacgtggtgc acagggacca ccaggtgctg ctggattccc tggagcagct      960
ggtagagtcg gaccacctgg tctacagggt aaccctggtc caccaggacc gcctggtcca     1020
gctgaaaagg acgggcccaa gggtgcaaga ggggatgccg gtcctccagg tagagccggt     1080
gagcctggtt tgcaaggtcc cgctggtcca cctggtgaga agggtgaacc aggtgatgac     1140
gggcctcctg gagccgaagg accgccaggt ccccagggac ttgctggaca gcgtggtatc     1200
gtgggattgc ctgggcaaag aggtgaaagg ggtttccctg gtttacctgg gccagctgga     1260
gagccaggga aacaaggagc acccggtgca gccggggata gaggaccacc gggtcctgtt     1320
ggtcctcccg gtttggctgg tcctgccgga gagcctggca gagagggtgg accgggtgct     1380
gacggcccac caggtcgaga tggggctgcc ggagtgaaag gtgataggag tgaggctgga     1440
gctgttggcg ctccaggagc cccaggtcca ccaggagctc cgggacctgc tggaccacct     1500
ggaccacaag gggacagggg cgaagcagga gctcaagggc cttaagcggc cgc            1553

<210> SEQ ID NO 6
<211> LENGTH: 1553
<212> TYPE: DNA
<213> ORGANISM: Artificial Sequence
<220> FEATURE:
<223> OTHER INFORMATION: polynucleotide #5

<400> SEQUENCE: 6
ctcgagaaaa gagaggctga agctgggccc aagggggcta ggggtcaacc aggagtaatg       60
ggctttcccg ggcctaaagg ggctaatggt gagcctggaa aagctggtga aagggacttt      120
ccaggtgctc caggtttgag agggctcccc ggaaaagatg gggaagctgg tgccgcagga      180
ccgccaggac cagccggccc cgcagggag agaggtgaac agggtgctcc aggtccgcca      240
ggtttccagg gtttacccgg ccctccagga cctccgggtg aaggtggtaa gccaggagat      300
cagggagttc caggtgaagc tggagctcct ggtttggttg gtcctagagg cgaacgaggt      360
tttccgggcg aaagaggaaa gccaggcgct cagggtctac aaggtcctcg tggactgccc      420
ggtgctcctg gaaagacgg cccaaaaggt gccgctggac ccgctggtcc acccggagca      480
caaggccctc ctggtctaca gggaatgccg ggagagagag gagctgccgg tatagctggt      540
cctaaaggtg acagaggga tgtgggtgag aagggaccag aaggcgctcc aggcaaggat      600
ggcggtagag gtttgggagg acctattggt cctccgggtc ccgctggagc taacggtgag      660
aagggcgaag tgggaccacc tgggccggcc ggagcagctg gtgctagagg tgcaccaggt      720
gaaaggggag aaaagggtcc tcctgggcca gcaggctttg ctggaccacc cggcgctgac      780
ggccaaccag gcgccaaggg tgaacaagga gaagccggtc agaaaggtga tgccggagca      840
ccaggacctc aaggacctaa gggtgcacca gggcctcagg gtcctgccgg cgttgccggt      900
ccaaagggcg caagaggtgc tcaaggacca ccaggtgcag ctggattccc aggcgctgct      960
```

| | |
|---|---:|
| ggtagagtcg gaccacctgg tttgcaagga aacccagggc cgcctggtcc acctggacct | 1020 |
| gctggaaaag acggtcctaa gggtgcaaga ggagatgcag gaccaccagg aagagcaggg | 1080 |
| gaaccaggtc tgcagggtcc tgctggacca ccaggagaaa agggagagcc tggtgacgac | 1140 |
| ggaccaccag gagcagaggg tccacccggt ccccaaggac ttgctggcca agaggcatc | 1200 |
| gttggtttac cgggtcaaag gggcgagcgt ggtttccctg gtttgccagg ccccaaggt | 1260 |
| gaacccggga acagggagc tcctggagct aagggtgatc gtggaccacc aggtccagtc | 1320 |
| ggtccaccag gtcttgctgg tcctgccggt gaaccgggaa gggagggtgg accaggtgcc | 1380 |
| gacggtcctc caggtcgaga tggtgctgcc ggggtaaaag gtgatagagg cgagaaagga | 1440 |
| gctgttggag ccccctggagc cccaggtcct cccggtgcac ctggtcctgc cgggcctccc | 1500 |
| ggtcctcaag gagatcgtgg agaggctgga gcccaagggc cttaagcggc cgc | 1553 |

<210> SEQ ID NO 7
<211> LENGTH: 1967
<212> TYPE: DNA
<213> ORGANISM: Artificial Sequence
<220> FEATURE:
<223> OTHER INFORMATION: polynucleotide #6

<400> SEQUENCE: 7

| | |
|---|---:|
| ctcgagaaaa gagaggctga agctatgggc tttcctggac ctaagggtgc aaacggagaa | 60 |
| ccgggaaagg caggcgagaa agggcttcct ggagctccag gttgcgtgg tttgccggt | 120 |
| aaggacggag aagctggtgc cgccgggcct ccgggtcctg ctggcccagc tggagaacgt | 180 |
| ggtgaacagg gtgccccagg aacctcctgga tttcaggggt tacccggccc accagggcca | 240 |
| cccggtgaag gaggtaaacc tggcgatcaa ggagtccccg gtgaggctgg agctccaggt | 300 |
| ttagtcggtc ctaggggaga gagaggtttc cctggagaaa gaggtaaacc aggagcccaa | 360 |
| ggcttgcagg ggccacgtgg acttccaggc gcacctggta agatggacc caaaggagct | 420 |
| gctggtccag ccggtcctcc gggtgcacaa gtccaccag gactgcaagg catgcccgga | 480 |
| gaaagaggtg ccgctggtat agctggacct aagggtgatc gaggggacgt cggtgaaaag | 540 |
| ggaccagaag gtgccccagg gaaagatgga ggaagaggtt tgggaggccc aattggccct | 600 |
| cccgggcccg ctggagccaa tggtgaaaag ggtgaggtag gtcctcctgg tccggccggt | 660 |
| gctgccggtg caagaggtgc acctggtgag agaggcgaga aggtccgcc cggcccagct | 720 |
| ggattcgctg gtccacccgg tgcagacggc caaccaggtg caaagggaga gcagggtgag | 780 |
| gctggccaga aaggtgatgc tggtgcacca ggtccacaag gtccaaaagg agctccaggt | 840 |
| cctcaaggac cagccggtgt agctggacca aagggcgcta gaggtgctca gggtcctcct | 900 |
| ggggctgctg gattcccagg tgctgctgga agagttggcc caccaggttt gcaaggtaac | 960 |
| ccagggcctc caggggcctcc cggccccgct ggtaaggacg tcctaaagg tgctagaggt | 1020 |
| gacgctggtc cgcctggtag agcaggagaa cctggattac agggaccagc cgggcctcca | 1080 |
| ggcgagaagg gtgaaccagg agatgatggt cctcccggcg ctgagggacc accaggacca | 1140 |
| caagggctag ctggtcaaag aggtatcgtg ggattgcctg gacagagagg tgaaaggggt | 1200 |
| tttccaggac tgccgggtcc taaaggagaa ccaggaaaac aaggtgcccc tggtgcaaag | 1260 |
| ggtgacaggg gaccgccagg accggttggt ccccaggtc ttgctggtcc tgctggtgag | 1320 |
| cctggaagag aaggtggacc aggagctgat ggaccgccag gcagagatgg agctgccgga | 1380 |
| gttaaaggtg accgagggga gaaggtgcc gttgggccc ctggtgcacc tggtccacca | 1440 |
| ggcgcaccag gccccgctgg aacctccggga ccccaaggtg atagaggtga agctggtgcc | 1500 |

-continued

```
caaggcccca tgggatttcc aggaccaaag ggagctaatg agaacccgg caaggccggt    1560 gagaaaggtt tgccaggtgc tcctggactt aggggactgc cgggaaagga tggcgaagcc    1620
ggagctgccg gtccaccagg tcctgctgga cccgcagggg agagaggcga acaaggagca    1680
cccggtcctc ctggattcca aggtttacca ggccctcccg gaccacctgg tgaaggaggt    1740
aaacctggcg accagggagt tcctggtgaa gccggtgctc ctgggttggt gggcccacga    1800
ggggagcgtg ggtttccagg agagcgtggt aagcctggtg cacaaggttt gcaaggccca    1860
agaggtctgc caggagcacc aggaaaggat ggacctaaag gtgcagctgg tccagctggg    1920
cctcctggtg cacagggtcc tccaggacta cagggtaag cggccgc                  1967
```

<210> SEQ ID NO 8
<211> LENGTH: 666
<212> TYPE: PRT
<213> ORGANISM: Artificial Sequence
<220> FEATURE:
<223> OTHER INFORMATION: RCP#7

<400> SEQUENCE: 8

```
Gly Pro Gln Gly Ala Arg Gly Gln Gly Val Met Gly Phe Pro Gly
1               5                   10                  15

Pro Lys Gly Ala Asn Gly Glu Pro Gly Lys Ala Gly Glu Lys Gly Leu
                20                  25                  30

Pro Gly Ala Pro Gly Leu Arg Gly Leu Pro Gly Lys Asp Gly Glu Ala
            35                  40                  45

Gly Ala Ala Gly Pro Pro Gly Pro Ala Gly Pro Ala Gly Glu Arg Gly
        50                  55                  60

Glu Gln Gly Ala Pro Gly Pro Pro Gly Phe Gln Gly Leu Pro Gly Pro
65                  70                  75                  80

Pro Gly Pro Pro Gly Glu Gly Lys Pro Gly Asp Gln Gly Val Pro
                85                  90                  95

Gly Glu Ala Gly Ala Pro Gly Leu Val Gly Pro Arg Gly Glu Arg Gly
            100                 105                 110

Phe Pro Gly Glu Arg Gly Lys Pro Gly Ala Gln Gly Leu Gln Gly Pro
        115                 120                 125

Arg Gly Leu Pro Gly Ala Pro Gly Lys Asp Gly Pro Lys Gly Ala Ala
    130                 135                 140

Gly Pro Ala Gly Pro Pro Gly Ala Gln Gly Pro Gly Leu Gln Gly
145                 150                 155                 160

Met Pro Gly Glu Arg Gly Ala Ala Gly Ile Ala Gly Pro Lys Gly Asp
                165                 170                 175

Arg Gly Asp Val Gly Glu Lys Gly Pro Glu Gly Ala Pro Gly Lys Asp
            180                 185                 190

Gly Gly Arg Gly Leu Gly Gly Pro Ile Gly Pro Pro Gly Pro Ala Gly
        195                 200                 205

Ala Asn Gly Glu Lys Gly Glu Val Gly Pro Pro Gly Pro Ala Gly Ala
    210                 215                 220

Ala Gly Ala Arg Gly Ala Pro Gly Glu Arg Gly Glu Lys Gly Pro Pro
225                 230                 235                 240

Gly Pro Ala Gly Phe Ala Gly Pro Pro Gly Ala Asp Gly Gln Pro Gly
                245                 250                 255

Ala Lys Gly Glu Gln Gly Glu Ala Gly Gln Lys Gly Asp Ala Gly Ala
            260                 265                 270

Pro Gly Pro Gln Gly Pro Lys Gly Ala Pro Gly Pro Gln Gly Pro Ala
```

```
                275                 280                 285
Gly Val Ala Gly Pro Lys Gly Arg Gly Ala Gln Gly Pro Pro Gly
            290                 295                 300
Ala Ala Gly Phe Pro Gly Ala Ala Gly Arg Val Gly Pro Pro Gly Leu
305                 310                 315                 320
Gln Gly Asn Pro Gly Pro Gly Pro Pro Gly Pro Ala Gly Lys Asp
            325                 330                 335
Gly Pro Lys Gly Ala Arg Gly Asp Ala Gly Pro Pro Gly Arg Ala Gly
                340                 345                 350
Glu Pro Gly Leu Gln Gly Pro Ala Gly Pro Pro Gly Glu Lys Gly Glu
                355                 360                 365
Pro Gly Asp Asp Gly Pro Pro Gly Ala Glu Gly Pro Pro Gly Pro Gln
370                 375                 380
Gly Leu Ala Gly Gln Arg Gly Ile Val Gly Leu Pro Gly Gln Arg Gly
385                 390                 395                 400
Glu Arg Gly Phe Pro Gly Leu Pro Gly Pro Lys Gly Glu Pro Gly Lys
                405                 410                 415
Gln Gly Ala Pro Gly Ala Lys Gly Asp Arg Gly Pro Pro Gly Pro Val
                420                 425                 430
Gly Pro Pro Gly Leu Ala Gly Pro Ala Gly Glu Pro Gly Arg Glu Gly
            435                 440                 445
Gly Pro Gly Ala Asp Gly Pro Pro Gly Arg Asp Gly Ala Ala Gly Val
            450                 455                 460
Lys Gly Asp Arg Gly Glu Lys Gly Ala Val Gly Ala Pro Gly Ala Pro
465                 470                 475                 480
Gly Pro Pro Gly Ala Pro Gly Pro Ala Gly Pro Gly Pro Gln Gly
                485                 490                 495
Asp Arg Gly Glu Ala Gly Ala Gln Gly Pro Gly Pro Gln Gly Ala Arg
            500                 505                 510
Gly Gln Pro Gly Val Met Gly Phe Pro Gly Pro Lys Gly Ala Asn Gly
            515                 520                 525
Glu Pro Gly Lys Ala Gly Glu Lys Gly Leu Pro Gly Ala Pro Gly Leu
530                 535                 540
Arg Gly Leu Pro Gly Lys Asp Gly Glu Ala Gly Ala Ala Gly Pro Pro
545                 550                 555                 560
Gly Pro Ala Gly Pro Ala Gly Glu Arg Gly Glu Gln Gly Ala Pro Gly
                565                 570                 575
Pro Pro Gly Phe Gln Gly Leu Pro Gly Pro Pro Gly Pro Pro Gly Glu
                580                 585                 590
Gly Gly Lys Pro Gly Asp Gln Gly Val Pro Gly Glu Ala Gly Ala Pro
            595                 600                 605
Gly Leu Val Gly Pro Arg Gly Glu Arg Gly Phe Pro Gly Glu Arg Gly
            610                 615                 620
Lys Pro Gly Ala Gln Gly Leu Gln Gly Pro Arg Gly Leu Pro Gly Ala
625                 630                 635                 640
Pro Gly Lys Asp Gly Pro Lys Gly Ala Ala Gly Pro Ala Gly Pro Pro
                645                 650                 655
Gly Ala Gln Gly Pro Pro Gly Leu Gln Gly
            660                 665

<210> SEQ ID NO 9
<211> LENGTH: 690
<212> TYPE: PRT
<213> ORGANISM: Artificial Sequence
```

<220> FEATURE:
<223> OTHER INFORMATION: RCP#2

<400> SEQUENCE: 9

Pro Gly Glu Arg Gly Ala Ala Gly Ile Ala Gly Pro Lys Gly Asp Arg
1               5                   10                  15

Gly Asp Val Gly Glu Lys Gly Pro Glu Ala Pro Gly Lys Asp Gly
            20                  25                  30

Gly Arg Gly Leu Gly Gly Pro Ile Gly Pro Pro Gly Pro Ala Gly Ala
            35                  40                  45

Asn Gly Glu Lys Gly Glu Val Gly Pro Pro Gly Pro Ala Gly Ala Ala
            50                  55                  60

Gly Ala Arg Gly Ala Pro Gly Glu Arg Gly Glu Lys Gly Pro Pro Gly
65                  70                  75                  80

Pro Ala Gly Phe Ala Gly Pro Pro Gly Ala Asp Gly Gln Pro Gly Ala
                85                  90                  95

Lys Gly Glu Gln Gly Glu Ala Gly Gln Lys Gly Asp Ala Gly Ala Pro
                100                 105                 110

Gly Pro Gln Gly Pro Lys Gly Ala Pro Gly Pro Gln Gly Pro Ala Gly
                115                 120                 125

Val Ala Gly Pro Lys Gly Ala Arg Gly Ala Gln Gly Pro Pro Gly Ala
130                 135                 140

Ala Gly Phe Pro Gly Ala Ala Gly Arg Val Gly Pro Pro Gly Leu Gln
145                 150                 155                 160

Gly Asn Pro Gly Pro Pro Gly Pro Pro Gly Pro Ala Gly Lys Asp Gly
                165                 170                 175

Pro Lys Gly Ala Arg Gly Asp Ala Gly Pro Pro Gly Arg Ala Gly Glu
                180                 185                 190

Pro Gly Leu Gln Gly Pro Ala Gly Pro Pro Gly Glu Lys Gly Glu Pro
                195                 200                 205

Gly Asp Asp Gly Pro Pro Gly Ala Glu Gly Pro Pro Gly Pro Gln Gly
                210                 215                 220

Leu Ala Gly Gln Arg Gly Ile Val Gly Leu Pro Gly Gln Arg Gly Glu
225                 230                 235                 240

Arg Gly Phe Pro Gly Leu Pro Gly Pro Lys Gly Glu Pro Gly Lys Gln
                245                 250                 255

Gly Ala Pro Gly Ala Lys Gly Asp Arg Gly Pro Pro Gly Pro Val Gly
                260                 265                 270

Pro Pro Gly Leu Ala Gly Pro Ala Gly Glu Pro Gly Arg Glu Gly Gly
                275                 280                 285

Pro Gly Ala Asp Gly Pro Pro Gly Arg Asp Gly Ala Ala Gly Val Lys
                290                 295                 300

Gly Asp Arg Gly Glu Lys Gly Ala Val Gly Ala Pro Gly Ala Pro Gly
305                 310                 315                 320

Pro Pro Gly Ala Pro Gly Pro Ala Gly Pro Gly Pro Gln Gly Asp
                325                 330                 335

Arg Gly Glu Ala Gly Ala Gln Gly Pro Pro Gly Glu Arg Gly Ala Ala
                340                 345                 350

Gly Ile Ala Gly Pro Lys Gly Asp Arg Gly Asp Val Gly Glu Lys Gly
                355                 360                 365

Pro Glu Gly Ala Pro Gly Lys Asp Gly Gly Arg Gly Leu Gly Gly Pro
                370                 375                 380

Ile Gly Pro Pro Gly Pro Ala Gly Ala Asn Gly Glu Lys Gly Glu Val
385                 390                 395                 400

-continued

```
Gly Pro Pro Gly Pro Ala Gly Ala Gly Ala Arg Gly Ala Pro Gly
                405                 410                 415
Glu Arg Gly Glu Lys Gly Pro Gly Pro Ala Gly Phe Ala Gly Pro
            420                 425                 430
Pro Gly Ala Asp Gly Gln Pro Gly Ala Lys Gly Glu Gln Gly Glu Ala
        435                 440                 445
Gly Gln Lys Gly Asp Ala Gly Ala Pro Gly Pro Gln Gly Pro Lys Gly
    450                 455                 460
Ala Pro Gly Pro Gln Gly Pro Ala Gly Val Ala Gly Pro Lys Gly Ala
465                 470                 475                 480
Arg Gly Ala Gln Gly Pro Pro Gly Ala Ala Gly Phe Pro Gly Ala Ala
                485                 490                 495
Gly Arg Val Gly Pro Pro Gly Leu Gln Gly Asn Pro Gly Pro Pro Gly
            500                 505                 510
Pro Pro Gly Pro Ala Gly Lys Asp Gly Pro Lys Gly Ala Arg Gly Asp
        515                 520                 525
Ala Gly Pro Pro Gly Arg Ala Gly Glu Pro Gly Leu Gln Gly Pro Ala
    530                 535                 540
Gly Pro Pro Gly Glu Lys Gly Glu Pro Gly Asp Asp Gly Pro Pro Gly
545                 550                 555                 560
Ala Glu Gly Pro Pro Gly Pro Gln Gly Leu Ala Gly Gln Arg Gly Ile
                565                 570                 575
Val Gly Leu Pro Gly Gln Arg Gly Glu Arg Gly Phe Pro Gly Leu Pro
            580                 585                 590
Gly Pro Lys Gly Glu Pro Gly Lys Gln Gly Ala Pro Gly Ala Lys Gly
        595                 600                 605
Asp Arg Gly Pro Pro Gly Pro Val Gly Pro Pro Gly Leu Ala Gly Pro
    610                 615                 620
Ala Gly Glu Pro Gly Arg Glu Gly Pro Gly Ala Asp Gly Pro Pro
625                 630                 635                 640
Gly Arg Asp Gly Ala Ala Gly Val Lys Gly Asp Arg Gly Glu Lys Gly
                645                 650                 655
Ala Val Gly Ala Pro Gly Ala Pro Gly Pro Pro Gly Ala Pro Gly Pro
            660                 665                 670
Ala Gly Pro Pro Gly Pro Gln Gly Asp Arg Gly Glu Ala Gly Ala Gln
        675                 680                 685
Gly Pro
    690

<210> SEQ ID NO 10
<211> LENGTH: 2033
<212> TYPE: DNA
<213> ORGANISM: Artificial Sequence
<220> FEATURE:
<223> OTHER INFORMATION: polynucleotide #7

<400> SEQUENCE: 10
ctcgagaaaa gagaggctga agctggcccg caaggggcca ggggtcagcc aggtgttatg      60
ggtttccccg gtcctaaggg cgctaacggg gagccaggta agcaggcga gaagggactt     120 cctggagcac caggtctaag aggattgcca gggaaggatg gcgaggcagg cgctgccggg     180
cctcctggtc ccgctggccc tgctggagaa agaggtgaac aaggagctcc tggacctccc     240
ggttttcagg gacttccggg accacccggc cctcctggtg aaggtggtaa accaggtgac     300
caaggcgtac caggcgaggc cggagcaccg ggacttgtcg gaccaagagg cgagcgagga     360
```

```
ttccccggtg agcgaggtaa gccgggagct caaggattgc aaggtccacg aggtctgcca      420
ggagcacctg ggaaagatgg accaaaagga gctgctggtc ctgctgggcc tccaggtgct      480
caaggtccac cgggtttgca gggcatgcct ggagaaaggg gcgctgctgg tatagctggt      540
cccaaaggtg accgtggtga tgttggtgaa aagggtccag aaggtgctcc cggtaaggac      600
ggaggtagag ggttaggcgg accaattggc cctccagggc ctgcaggtgc aatggagag       660 aagggagaag tgggtccacc gggcccagcc ggcgctgctg tgctagagg tgcccctggg       720 gagagggtg agaagggacc gccaggacca gctggatttg caggacctcc cggagcagat       780
ggccagccag gtgcaaaggg tgaacaaggg gaagctggac agaagggaga tgccggcgca      840
cccggaccac aaggtccaaa aggagcccca ggtccacagg gtccagctgg tgtcgcaggc      900
cctaaaggtg ctagaggcgc tcaaggccct ccaggagctg ccggtttccc tggtgctgct      960
ggcagagtag gccaccagg tttacaagga atccagggc ctcctggtcc accaggacct       1020
gcaggaaaag atggtcccaa aggagcaaga ggtgacgcag acctccagg aagagctggg       1080 gagccagggc ttcaaggtcc ggccggtccg ccgggtgaga agggagaacc aggtgacgac      1140
ggtccaccag gggctgaggg tcctcctggt cctcaggggc tagctggtca agaggtatc      1200 gttggactgc caggtcagcg tggtgaacgt ggtttccctg gtttgcctgg tcctaaaggg      1260
gaacctggta acaaggcgc cccgggagct aagggcgata ggggacctcc tggaccggtt      1320
ggtccaccag gtctggccgg tcctgctgga gaaccaggtc gtgaaggagg accggtgct      1380 gacgaccac caggtagaga tggtcagccc ggggttaaag gagacagagg tgaaaaggga      1440
gctgtgggcg ctcccggggc cccaggacca ccaggcgcac caggacccgc tggtccccc       1500 ggtccccaag gtgatagagg tgaagccggt gctcaaggac ctggtcctca aggagccaga      1560
ggacagcctg gtgtgatggg atttcctgga cctaaaggtg caaacggaga gcctggaaaa      1620
gccggagaga agggtttacc aggagctccc gggttgagag gattgccgg taagatgga       1680 gaagctggtg ctgctggccc accaggtcca gccggacctg caggcgagag ggtgaacag       1740 ggagctccag gacctcctgg gtttcaagga ttgcctggcc ctccgggtcc accaggagag      1800
ggtggtaagc caggggatca gggcgttcca ggtgaagctg tgcacccgg tttggtcggt      1860 cctagagggg aaagaggatt tcccgggaa cgtggaaagc caggtgccca aggtctgcaa      1920
ggtccaagag gtttaccagg tgctcccgga aaggatggac ctaagggtgc cgccggtccc      1980
gctggtcctc ctggagcaca gggaccacct ggtttgcaag gataagcggc cgc             2033
```

<210> SEQ ID NO 11
<211> LENGTH: 2105
<212> TYPE: DNA
<213> ORGANISM: Artificial Sequence
<220> FEATURE:
<223> OTHER INFORMATION: polynucleotide #2

<400> SEQUENCE: 11

```
ctcgagaaaa gagaggctga agctcctggt gagcgtggcg ctgctggcat tgccggtcct       60
aaaggcgata gaggcgatgt cggagagaag ggccctgaag gtgcacccgg caaagacgga      120
ggaagaggac tgggtggtcc aataggtccg ccaggtccag caggagccaa tggcgagaaa      180 ggagagggttg gtccaccagg tcctgctggt gctgccggtg ctcgtggagc ccctggagaa      240
cgaggtgaaa agggtccgcc aggaccagca ggctttgccg gaccaccagg agccgacggt      300
caacctggag caaagggtga acagggtgaa gctggtcaga gggtgatgc tggagctcca       360
```

```
ggaccgcaag ggccaaaagg tgctcctggc ccacaaggtc cagctggtgt cgcaggacct      420
aaaggtgcta ggggagccca aggtcctcca ggggctgccg ggtttcctgg cgctgctggg      480
agagtagggc ctccaggcct ccaaggtaac cctgggccac ctggtccacc tggccctgct      540
gggaaggacg gaccaaaagg agccagaggt gatgctggtc cacctggtag agctggtgaa      600
ccaggacttc aagggcccgc tggtcctccc ggagagaagg gagaacccgg agatgatggt      660
cctcctggtg cagaaggacc tccagggccc caagggctag caggccagag aggaatcgtg      720
ggattgccag acaacgtggt gagagggga ttccccggtt tacccggtcc gaaaggggaa      780
cccggaaagc agggtgctcc aggcgccaaa ggagacagag gtccgcctgg gcctgttgga      840
ccacccggtt tggctggtcc ggcaggagag ccaggtcgag aaggtggccc aggtgccgat      900
ggtcctccag gtagagatgg cgctgccggt gtgaagggag acagaggaga aagggagca      960 gttggtgctc caggtgctcc tggaccgccc ggtgcacctg gtcctgctgg accaccagga     1020
ccacagggag acagaggtga agctggtgca caaggtcccc ctggtgagcg tggcgctgct     1080
ggcattgccg gtcctaaagg cgatagaggc gatgtcggag agaagggccc tgaaggtgca     1140
cccggcaaag acggaggaag aggactgggt ggtccaatag gtccgccagg tccagcagga     1200
gccaatggcg agaaaggaga ggttggtcca ccaggtcctg ctggtgctgc cggtgctcgt     1260
ggagcccctg gagaacgagg tgaaaagggt ccgccaggac cagcaggctt gccggacca      1320 ccaggagccg acggtcaacc tggagcaaag ggtgaacagg gtgaagctgg tcagaagggt     1380
gatgctggag ctccaggacc gcaagggcca aaaggtgctc ctggcccaca aggtccagct     1440
ggtgtcgcag gacctaaagg tgctagggga gcccaaggtc ctccaggggc tgccgggttt     1500
cctggcgctg ctgggagagt agggcctcca ggcctccaag gtaaccctgg gccacctggt     1560
ccacctggcc ctgctgggaa ggacggacca aaaggagcca gaggtgatgc tggtccacct     1620
ggtagagctg gtgaaccagg acttcaaggg cccgctggtc ctcccggaga aagggagaa     1680 cccggagatg atggtcctcc tggtgcagaa ggacctccag ggccccaagg gctagcaggc     1740
cagagaggaa tcgtgggatt gccaggacaa cgtggtgaga ggggattccc cggtttaccc     1800
ggtccgaaag gggaacccgg aaagcagggt gctccaggcg ccaaaggaga cagaggtccg     1860
cctgggcctg ttggaccacc cggtttggct ggtccggcag gagagccagg tcgagaaggt     1920 ggccaggtg ccgatggtcc tccaggtaga gatggcgctg ccggtgtgaa gggagacaga     1980
ggagagaagg gagcagttgg tgctccaggt gctcctggac cgcccggtgc acctggtcct     2040
gctggaccac caggaccaca gggagacaga ggtgaagctg gtgcacaagg tccctaagcg     2100
gccgc                                                                 2105

<210> SEQ ID NO 12
<211> LENGTH: 6
<212> TYPE: PRT
<213> ORGANISM: Artificial Sequence
<220> FEATURE:
<223> OTHER INFORMATION: GFPGER

<400> SEQUENCE: 12

Gly Phe Pro Gly Glu Arg
1               5

<210> SEQ ID NO 13
<211> LENGTH: 6
<212> TYPE: PRT
<213> ORGANISM: Artificial Sequence
<220> FEATURE:
```

```
<223> OTHER INFORMATION: GVMGFP

<400> SEQUENCE: 13

Gly Val Met Gly Phe Pro
1               5

<210> SEQ ID NO 14
<211> LENGTH: 4
<212> TYPE: PRT
<213> ORGANISM: Artificial Sequence
<220> FEATURE:
<223> OTHER INFORMATION: REDV

<400> SEQUENCE: 14

Arg Glu Asp Val
1

<210> SEQ ID NO 15
<211> LENGTH: 5
<212> TYPE: PRT
<213> ORGANISM: Artificial Sequence
<220> FEATURE:
<223> OTHER INFORMATION: YIGSR

<400> SEQUENCE: 15

Tyr Ile Gly Ser Arg
1               5

<210> SEQ ID NO 16
<211> LENGTH: 5
<212> TYPE: PRT
<213> ORGANISM: Artificial Sequence
<220> FEATURE:
<223> OTHER INFORMATION: PDSG R

<400> SEQUENCE: 16

Pro Asp Ser Gly Arg
1               5

<210> SEQ ID NO 17
<211> LENGTH: 7
<212> TYPE: PRT
<213> ORGANISM: Artificial Sequence
<220> FEATURE:
<223> OTHER INFORMATION: RYVVLPR

<400> SEQUENCE: 17

Arg Tyr Val Val Leu Pro Arg
1               5

<210> SEQ ID NO 18
<211> LENGTH: 6
<212> TYPE: PRT
<213> ORGANISM: Artificial Sequence
<220> FEATURE:
<223> OTHER INFORMATION: LGTIPG

<400> SEQUENCE: 18

Leu Gly Thr Ile Pro Gly
1               5

<210> SEQ ID NO 19
<211> LENGTH: 10
<212> TYPE: PRT
<213> ORGANISM: Artificial Sequence
<220> FEATURE:
<223> OTHER INFORMATION: RNIAEIIKDI
```

```
<400> SEQUENCE: 19

Arg Asn Ile Ala Glu Ile Ile Lys Asp Ile
1               5                   10

<210> SEQ ID NO 20
<211> LENGTH: 5
<212> TYPE: PRT
<213> ORGANISM: Artificial Sequence
<220> FEATURE:
<223> OTHER INFORMATION: IKVAV

<400> SEQUENCE: 20

Ile Lys Val Ala Val
1               5

<210> SEQ ID NO 21
<211> LENGTH: 4
<212> TYPE: PRT
<213> ORGANISM: Artificial Sequence
<220> FEATURE:
<223> OTHER INFORMATION: DGEA

<400> SEQUENCE: 21

Asp Gly Glu Ala
1
```

POLYPEPTIDE, SCAFFOLD COMPOSITION, COMPOSITION FOR CARTILAGE TISSUE RESTORATION, COMPOSITION FOR CARTILAGE CELL CULTURE, AND COMPOSITION FOR PROMOTING GLYCOSAMINOGLYCAN PRODUCTION

CROSS-REFERENCE TO RELATED APPLICATIONS

This application is a continuation application of International Application No. PCT/JP2013/075946, filed Sep. 25, 2013, the disclosure of which is incorporated herein by reference in its entirety. Further, this application claims priority from Japanese Patent Application No. 2012-213110 filed on Sep. 26, 2012, the disclosure of which is incorporated herein by reference in its entirety.

TECHNICAL FIELD

The present invention relates to a polypeptide, scaffold composition, composition for cartilage tissue restoration, composition for cartilage cell culture, and composition for promoting glycosaminoglycan production.

BACKGROUND ART

Currently, practical use of regenerative medicine, in which attempts are made to regenerate a body tissue or organ whose function is deteriorated or impaired, is being promoted. Regenerative medicine is a new medical technology in which a body tissue that cannot be recovered by the self-healing ability is reconstructed using three factors, that is, cells, scaffolds and growth factors, such that the tissue has a morphology and/or function similar to those of the original tissue.

In the field of regenerative medicine, collagen or gelatin, which has high biocompatibility, is used in some cases for the purpose of, for example, helping tissue repair or regeneration by cells. In particular, collagen or gelatin is sometimes used for regeneration of a tissue having a three-dimensional structure such as bone or skin, and, for the purpose of achieving better tissue regeneration, various modifications are being made for collagen and gelatin.

Cartilage, for example, articular cartilage, is a tissue composed of a very small amount (about 2%) of cartilage cells together with an extracellular matrix, and the extracellular matrix is known to contain about 70% water, about 20% collagen and about 10% proteoglycan. The proteoglycan in the extracellular matrix is a glycoprotein containing a polysaccharide called glycosaminoglycan (GAG) in an amount of about 95%, and about 5% protein. In a cartilage, cartilage cells are supported by being surrounded by collagen or proteoglycan produced by the cartilage cells themselves. In particular, glycosaminoglycan is thought to be a substance playing a role in keeping water in the cartilage matrix and involved in suppression of deterioration of, or in repair of, cartilage. Thus, studies are being carried out to develop a scaffold material for cartilage cells, which scaffold material allows favorable matrix production by the cartilage cells.

As a scaffold material for cartilage cells, natural form of type II collagen is conventionally used.

Japanese National-Phase Publication (JP-A) No. 2007-528699 discloses a cell support coated with an RGD-enriched gelatin-like protein with enhanced cell binding capacity, and describes that such a cell support can be used for skin grafting, wound healing, or enhancement of the growth (regeneration) of bone or cartilage.

WO 2008/133196 discloses a recombinant gelatin having an RGD sequence as a cell adhesion signal, and describes that such a gelatin can be used as a cell-adhesive matrix. WO 2008/133196 also describes that, in cases of cell therapy, a cell-adhesive matrix material that can be used as a scaffold for cells is generally preferred, and that, in cases of cartilage regeneration, a high-strength matrix is desirable.

SUMMARY OF INVENTION

Technical Problem

As described above, the GAG in the extracellular matrix is a matrix substance significantly involved in the metabolism of cartilage cells. However, natural form of type II collagen currently used shows only insufficient promotion of production of the extracellular matrix. Scaffold materials which promote matrix production by cartilage cells have not been conventionally known so far. Moreover, compositions for cartilag tissues restoration or compositions for cartilage cell culture, which can promote repair of cartilage tissues from the viewpoint of extracellular-matrix production, or compositions which can favorably promote cellular production of glycosaminoglycan among the extracellular matrix, have not been provided so far.

Accordingly, the invention aims to provide a scaffold composition excellent in promotion of extracellular-matrix production by cartilage cells, a composition for cartilage tissue restoration, a composition for cartilage cell culture, and a composition for promoting glycosaminoglycan production, and a material therefor.

Solution to Problem

The invention is as follows.

[1] A polypeptide having an amino acid sequence in which the number of RGD sequences contained per molecular weight of 10 kDa is not less than 0.30; the number of GFPGER (SEQ ID NO:12) sequences contained per molecular weight of 10 kDa is not less than 0.15; and the number of GVMGFP (SEQ ID NO:13) sequences contained per molecular weight of 10 kDa is less than 0.30.

[2] The polypeptide according to [1], wherein the number of amino acid residues in the full-length sequence is from 300 to 1400.

[3] The polypeptide according to [1] or [2], having an identity of not less than 85% to an amino acid sequence of natural form of human type II collagen.

[4] The polypeptide according to any one of [1] to [3], having a molecular weight of from 30 kDa to 80 kDa.

[5] The polypeptide according to any one of [1] to [4], having an isoelectric point (pI) of not more than 6.0.

[6] The polypeptide according to any one of [1] to [5], which is a recombinant peptide.

[7] A polypeptide which is (A) a polypeptide having the amino acid sequence of SEQ ID NO:1, 2, or 3;

(B) a polypeptide having the same amino acid sequence as the amino acid sequence of SEQ ID NO:1, 2, or 3 except that one or several amino acids are deleted, substituted and/or added, which polypeptide has a capacity to promote glycosaminoglycan production; or (C) a polypeptide having an amino acid sequence having a sequence identity of not less than 80% to the amino acid sequence of SEQ ID NO:1, 2, or 3, which polypeptide has a capacity to promote GAG production.

[8] A polypeptide having an amino acid sequence having a sequence identity of not less than 90% to the amino acid sequence of SEQ ID NO:1, 2, or 3, which polypeptide has a capacity to promote glycosaminoglycan production.

[9] A polypeptide having an amino acid sequence having a sequence identity of not less than 95% to the amino acid sequence of SEQ ID NO:1, 2, or 3, which polypeptide has a capacity to promote glycosaminoglycan production.

[10] A scaffold composition comprising the polypeptide according to any one of [1] to [9].

[11] A composition for cartilage tissue testoration, comprising the polypeptide according to any one of [1] to [9].

[12] A composition for cartilage cell culture, comprising the polypeptide according to any one of [1] to [9].

[13] A composition for promoting glycosaminoglycan production, comprising the polypeptide according to any one of [1] to [9].

[14] Use of the polypeptide according to any one of [1] to [9] in production of a scaffold composition.

[15] Use of the polypeptide according to any one of [1] to [9] in production of a composition for cartilage tissue restoration.

[16] Use of the polypeptide according to any one of [1] to [9] in production of a composition for cartilage cell culture.

[17] Use of the polypeptide according to any one of [1] to [9] in production of a composition for promoting glycosaminoglycan production

[18] A method for restoration of cartilage or regeneration of cartilage, comprising administering the composition for cartilage tissue restoration according to [11] to a damaged area of cartilage.

Advantageous Effects of Invention

By the invention, a scaffold composition excellent in promotion of extracellular-matrix production by cartilage cells, a composition for cartilage tissue restoration, a composition for cartilage cell culture, and a composition for promoting glycosaminoglycan production, and a material therefor can be provided.

BRIEF DESCRIPTION OF DRAWINGS

FIG. 1 is a graph showing the results of evaluation of the GAG production-promoting capacity of each polypeptide in Examples and Comparative Examples.

DESCRIPTION OF EMBODIMENTS

The polypeptide of the invention is a polypeptide having an amino acid sequence in which the number of RGD sequences contained per molecular weight of 10 kDa is not less than 0.30; the number of GFPGER (SEQ ID NO:12) sequences contained per molecular weight of 10 kDa is not less than 0.15; and the number of GVMGFP (SEQ ID NO:13) sequences contained per molecular weight of 10 kDa is less than 0.30.

In the invention, according to the above constitution, production of an extracellular matrix, especially glycosaminoglycan (which may be hereinafter referred to as GAG), by cartilage cells is promoted when the cartilage cells are in contact with the polypeptide according to the invention.

That is, in order to promote production of GAG more efficiently than natural form of type II collagen, not less than the predetermined numbers of RGD sequences and GFPGER (SEQ ID NO:12) sequences need to be present. In addition, the number of GVMGFP (SEQ ID NO:13) sequences needs to be 0, or not more than 0.30 per molecular weight of 10 kDa in the full-length polypeptide. In the invention, GAG production by cartilage cells is promoted by satisfaction of the conditions of the numbers of RGD sequences, GFPGER (SEQ ID NO:12) sequences, and GVMGFP (SEQ ID NO:13) sequences contained. It can be assumed that GAG may be present in a large amount in the vicinity of cartilage cells after contacting with the polypeptide according to the invention, and that excellent proliferation and growth of the cartilage cells may also be obtained thereby. However, the invention is not bound by these theories.

The polypeptide according to the invention may be hereinafter referred to as "specific polypeptide".

The invention is described below.

In the present description, the term "step" means not only an independent step, but also a step which cannot be clearly distinguished from other steps, as long as an expected object of the step can be achieved therewith.

In the present description, a numerical range indicated using "to" means the range in which the values described before and after "to" are included as the minimum value and the maximum value, respectively.

In the present description, the amount of each component in a composition means, in cases in which plural substances corresponding to the component are present in the composition, the total amount of the plural substances present in the composition, unless otherwise specified.

In the invention, each amino acid residue in an amino acid sequence may be represented by the single-letter code (for example, "G" represents a glycine residue) or three-letter code (for example, "Gly" represents a glycine residue), which are well known in the art.

In the invention, "%" as used in relation to the amino acid sequence of a polypeptide is based on the number of amino acid (or imino acid) residues, unless otherwise specified.

In the present description, the meaning of an expression such as "corresponding amino acid residue" as used for a specific amino acid residue in an amino acid sequence is as follows: when 2 or more amino acid sequences to be compared are aligned by a method well known in the art in consideration of insertions, deletions, and substitutions such that the number of identical amino acid residues becomes maximum, the amino acid residue, in another amino acid sequence, at the same position as the position of a specific amino acid residue in the amino acid sequence as a reference is the "corresponding amino acid residue".

In the invention, the "identity" between the amino acid sequences of two polypeptides to be compared means the value calculated by the following equation. Comparison of plural polypeptides (alignment) is carried out by an ordinary method such that the number of identical amino acid residues is maximum.

In judgment of the identity between recombinant peptides, each of the two polypeptides to be compared is separated into arbitrary fragments each having not less than 10 amino acid residues, and the correspondence of the fragments derived from one polypeptide to the fragments derived from the other polypeptide is determined such that the identity becomes maximum. The amino acid sequence is then compared between the corresponding fragments, to determine the identity as a whole. In a case in which repeated sequences (sequences each having not less than 10 amino acid residues) are contained, the second and later repeats are excluded before the determination of the identity (%) between the corresponding portions.

Identity (%)=[(Number of identical amino acid residues)/(Alignment length)]×100

[Specific Polypeptide]

The specific polypeptide according to the invention has an amino acid sequence in which the number of RGD sequences contained per molecular weight of 10 kDa is not less than 0.30; the number of GFPGER (SEQ ID NO:12) sequences contained per molecular weight of 10 kDa is not less than 0.15; and the number of GVMGFP (SEQ ID NO:13) sequences contained per molecular weight of 10 kDa is less than 0.30.

Since the specific polypeptide has an amino acid sequence containing the predetermined numbers of RGD sequences, GFPGER (SEQ ID NO:12) sequences, and GVMGFP (SEQ ID NO:13) sequences, the polypeptide can work as a favorable scaffold that promotes production of the matrix by cartilage cells.

The RGD sequence is known as an integrin-binding site or a sequence (motif) having a cell adhesion function. The number of RGD sequences contained in the specific polypeptide is not less than 0.30 per molecular weight of the specific polypeptide of 10 kDa. In cases in which the number is less than 0.30, the matrix production by cartilage cells cannot be sufficiently promoted. The number of RGD sequences contained in the specific polypeptide may also be not less than 0.35, or may be not less than 0.40. Although the upper limit of the number of RGD sequences contained in the specific polypeptide varies depending on the total length of the specific polypeptide, the number is, for example, preferably not more than 2.0, more preferably not more than 1.0, still more preferably not more than 0.5 per 10 kDa.

In cases in which plural RGD sequences are contained in the specific polypeptide, the number of amino acid residues between the RGD sequences is preferably from 0 to 100, more preferably from 25 to 60, although the number varies depending on the total length of the particular polypeptide. The RGD sequences are preferably unevenly distributed in the specific polypeptide such that the number of amino acid residues therebetween falls within the above ranges.

The GFPGER (SEQ ID NO:12) sequence is known as an α2β1 integrin-binding site or a sequence having a cell adhesion function. The number of GFPGER (SEQ ID NO:12) sequences contained in the specific polypeptide is not less than 0.15 per molecular weight of the specific polypeptide of 10 kDa. In cases in which the number is less than 0.15, the matrix production by cartilage cells cannot be sufficiently promoted. The number of GFPGER (SEQ ID NO:12) sequences contained in the specific polypeptide may also be not less than 0.20, or may be not less than 0.30. Although the upper limit of the number of GFPGER (SEQ ID NO:12) sequences contained in the specific polypeptide varies depending on the total length of the specific polypeptide, the number is, for example, preferably not more than 1.0, more preferably not more than 0.5 per 10 kDa.

"P" (proline residue) in the GFPGER (SEQ ID NO:12) sequences may also be an oxyproline residue.

The GVMGFP (SEQ ID NO:13) sequence is commonly found among fibrous collagen, and known as a recognition site of DDR-2 (Discoidin domain receptor-2). The GVMGFP (SEQ ID NO:13) sequence is also known to be involved in the proliferation of cells. The number of GVMGFP (SEQ ID NO:13) sequences contained in the specific polypeptide is less than 0.30 per molecular weight of the specific polypeptide of 10 kDa. In cases in which the number is not less than 0.30, the matrix production by cartilage cells cannot be sufficiently promoted. The number of GVMGFP (SEQ ID NO:13) sequences, if present, contained in the specific polypeptide may also be not more than 0.28, or may be not more than 0.25 per molecular weight of the particular polypeptide of 10 kDa. In terms of the lower limit of the number of GVMGFP (SEQ ID NO:13) sequences contained in the specific polypeptide, the number of the sequences may be, for example, not less than 0.2, or may be zero, per molecular weight of the specific polypeptide of 10 kDa.

From the viewpoint of promotion of the matrix production, the ratio of the number of RGD sequences contained to the total number of GFPGER (SEQ ID NO:12) sequences and GVMGFP (SEQ ID NO:13) sequences contained, that is, [number of RGD sequences contained/(total number of GFPGER (SEQ ID NO:12) sequences and GVMGFP (SEQ ID NO:13) sequences contained)] is preferably from 0.8 to 1.2, more preferably 1.

The positional relationship among the RGD sequences, GFPGER (SEQ ID NO:12) sequences, and GVMGFP (SEQ ID NO:13) sequences in the entire polypeptide is not limited as long as the ratios of these sequences present in the polypeptide satisfy the predetermined conditions described above. For example, a GVMGFP (SEQ ID NO:13) sequence may be placed either in the N-terminal side or C-terminal side of a GFPGER (SEQ ID NO:12) sequence. In cases in which plural RGD sequences are present, all of the RGD sequences may be placed between a GVMGFP (SEQ ID NO:13) sequence and the C-terminus of the polypeptide. In cases in which plural GFPGER (SEQ ID NO:12) sequences are present, all of the RGD sequences may be placed between the GFPGER (SEQ ID NO:12) sequence most close to the N-terminus and the GFPGER (SEQ ID NO:12) sequence most close to the C-terminus. Alternatively, at least one RGD sequence may be placed either in the N-terminal side of the GFPGER (SEQ ID NO:12) sequence most close to the N-terminus or in the C-terminal side of the GFPGER (SEQ ID NO:12) sequence most close to the C-terminus.

The specific polypeptide may contain, in addition to the RGD sequence(s), GFPGER (SEQ ID NO:12) sequence(s), and/or GVMGFP (SEQ ID NO:13) sequence(s), one or more other known sequences (motifs).

For example, the specific polypeptide may have repeats of a sequence(s) represented by Gly-X-Y. In cases in which plural Gly-X-Y sequences are present, the plural Gly-X-Y sequences may be either the same or different. In Gly-X-Y, Gly represents a glycine residue, and each of X and Y represents an arbitrary amino acid residue other than a glycine residue. A large number of imino acid residues, that is, proline residues and/or oxyproline residues, are preferably contained as X and Y. The ratio of the imino acid residues contained in the entire specific polypeptide is preferably from 10% to 45%. The ratio of Gly-X-Y contained in the entire specific polypeptide is preferably not less than 80%, more preferably not less than 95%, still more preferably not less than 99%.

The specific polypeptide may also contain one or more other cell adhesion signals from the viewpoint of biocompatibility. Examples of such cell adhesion signals include sequences such as the LDV sequence, REDV (SEQ ID NO:14)sequence, YIGSR (SEQ ID NO:15) sequence, PDSGR (SEQ ID NO:16) sequence, RYVVLPR (SEQ ID NO:17) sequence, LGTIPG (SEQ ID NO:18) sequence, RNIAEIIKDI (SEQ ID NO:19) sequence, IKVAV (SEQ ID NO:20) sequence, LRE sequence, DGEA (SEQ ID NO:21) sequence, and HAV sequence. Preferred examples of the cell adhesion signals include YIGSR (SEQ ID NO:15) sequence, PDSGR (SEQ ID NO:16) sequence, LGTIPG (SEQ ID NO:18) sequence, IKVAV (SEQ ID NO:20)sequence, and HAV sequence. These other cell adhesion signals may be used singly, or in combination of two or more kinds thereof.

The number of amino acid residues in the entire specific polypeptide is not limited as long as the 3 kinds of sequences described above are contained at the predetermined ratios. The number of amino acid residues in the entire particular polypeptide is preferably from 300 to 1400, more preferably from 400 to 1000, still more preferably from 500 to 800. In cases in which the number of amino acid residues is not less than 300, the effect of promoting the matrix production of cartilage cells tends to be more securely exerted, and, in cases in which the number of amino acid residues is not more than 1400, solubility of the polypeptide in water is not largely deteriorated, and the polypeptide tends to have excellent handling properties.

The molecular weight of the specific polypeptide is preferably from 30 kDa to 80 kDa, more preferably from 40 kDa to 70 kDa. With a molecular weight of not less than 30 kDa, the effect of promoting the matrix production of cartilage cells tends to be more securely exerted, and, with a molecular weight of not more than 80 kDa, solubility of the polypeptide in water is not largely deteriorated, and the polypeptide tends to have excellent handling properties. In the invention, the molecular weight of the specific polypeptide is a value measured by electrospray ionization mass spectrometry (ESI-MS) (Q-TOF PREMIER, manufactured by Waters Corporation) according to an ordinary method.

As long as the specific polypeptide has an amino acid sequence containing the predetermined numbers of RGD sequences, GFPGER sequences, and GVBMGFP sequences, the amino acid sequence of the remaining part is not limited. From the viewpoint of, for example, promotion of proliferation of cartilage cells, the identity to the amino acid sequence of natural form of collagen is preferably not less than 85%, more preferably not less than 90%, still more preferably not less than 95%, still more preferably not less than 98%.

Examples of the natural from of collagen to be used as the standard of identity include type I, type II, type III, type IV, and type V. From the viewpoint of promotion of cartilage matrix production, the identity to the amino acid sequence of natural from of human type II collagen may be preferably not less than 85%, more preferably not less than 90%, still more preferably not less than 95%, still more preferably not less than 98%.

Preferred examples of the origin of the natural from of collagen to be used as the standard of identity include human, horse, pig, mouse and rat. The origin of the natural from of collagen is more preferably human.

The natural from of collagen to be used as the standard of identity is more preferably native human type II collagen. A known example of the sequence of natural from of human type II collagen is the following amino acid sequence of SEQ ID NO:4. The amino acid sequence of natural from of human type II collagen is shown in Table 1. In Table 1, RGD, GFPGER (SEQ ID NO:12), and GVMGFP (SEQ ID NO:13) sequences are indicated in bold.

TABLE 1

| Collagen II human alpha I (1487 a.a.) (SEQ ID NO: 4) |
|---|
| MIRLGAPQTL VLLTLLVAAV LRCQGQDVQE AGSCVQDGQR YNDKDVWKPE PCRICVCDTG |
| TVLCDDIICE DVKDCLSPEI PFGECCPICP TDLATASGQP GPKGQKGEPG DIKDIVGPKG |
| PPGPQGPAGE QGPRGDRGDK GEKGAPGPRP RDGEPGTPGN PGPPGPPGPP GPPGLGGNFA |
| AQMAGGFDEK AGGAQLGVMQ GPMGPMGPRG PPGPAGAPGP QGFQGNPGEP GEPGVSGPMG |
| PRGPPGPPGK PGDDGEAGKP GKAGERGPPG PQGARGFPGT PGLPGVKGHR GYPGLDGAKG |
| EAGAPGVKGE SGSPGENGSP GPMGPRGLPG ERGRTGPAGA AGARGNDGQP GPAGPPGPVG |
| PAGGPGFPGA PGAKGEAGPT GARGPEGAQG PRGEPGTPGS PGPAGASGNP GTDGIPGAKG |
| SAGAPGIAGA PGFPGPRGPP GPQGATGPLG KPGQTGEPGI AGFKGEQGPK GEPGPAGPQG |
| APGPAGEEGK RGARGEPGGV GPIGPPGERG APGNRGFPGQ DGLAGPKGAP GERGPSGLAG |
| PKGANGDPGR PGEPGLPGAR GLTGRPGDAG PQGKVGPSGA PGEDGRPGPP GPQGARGQPG |
| VMGFPGPKGA NGEPGKAGEK GLPGAPGLRG LPGKDGETGA AGPPGPAGPA GERGEQGAPG |
| PSGFQGLPGP PGPPGEGGKP GDQGVPGEAG APGLVGPRGE RGFPGERGSP GAQGLQGPRG |
| LPGTPGTDGP KGASGPAGPP GAQGPPGLQG MPGERGAAGI AGPKGDRGDV GEKGPEGAPG |
| KDGGRGLTGP IGPPGPAGAN GEKGEVGPPG PAGSAGARGA PGERGETGPP GPAGFAGPPG |
| ADGQPGAKGE QGEAGQKGDA GAPGPQGPSG APGPQGPTGV TGPKGARGAQ GPPGATGFPG |
| AAGRVGPPGS NGNPGPPGPP GPSGKDGPKG ARGDSGPPGR AGEPGLQGPA GPPGEKGEPG |
| DDGPSGAEGP PGPQGLAGQR GIVGLPGQRG ERGFPGLPGP SGEPGKQGAP GASGDRGPPG |
| PVGPPGLTGP AGEPGREGSP GADGPPGRDG AAGVKGDRGE TGAVGAPGAP GPPGSPGPAG |
| PTGKQGDRGE AGAQGPMGPS GPAGARGIQG PQGPRGDKGE AGEPGERGLK GHRGFTGLQG |
| LPGPPGPSGD QGASGPAGPS GPRGPPGPVG PSGKDGANGI PGPIGPPGPR GRSGETGPAG |

TABLE 1 -continued

Collagen II human alpha I (1487 a.a.) (SEQ ID NO: 4)

```
PPGNPGPPGP PGPPGPGIDM SAFAGLGPRE KGPDPLQYMR ADQAAGGLRQ HDAEVDATLK

SLNNQIESIR SPEGSRKNPA RTCRDLKLCH PEWKSGDYWI DPNQGCTLDA MKVFCNMETG

ETCVYPNPAN VPKKNWWSSK SKEKKHIWFG ETINGGFHFS YGDDNLAPNT ANVQMTFLRL

LSTEGSQNIT YHCKNSIAYL DEAAGNLKKA LLIQGSNDVE IRAEGNSRFT YTALKDGCTK

HTGKWGKTVI EYRSQKTSRL PIIDIAPMDI GGPEQEFGVD IGPVCFL
```

The isoelectric point (pI) of the specific polypeptide is not limited, and may be, for example, not more than 10.0. The isoelectric point is preferably not more than 9.2, more preferably not more than 7.0, still more preferably not more than 6.0 from the viewpoint of promotion of proliferation of cartilage cells. In terms of the lower limit of the isoelectric point, the isoelectric point may be, for example, not less than 5.0. The pI of the polypeptide may be adjusted by an ordinary method. For example, the pI can be lowered by increasing the content of neutral amino acid residues (for example, glycine residues and alanine residues) and/or acidic amino acid residues (glutamic acid residues and aspartic acid residues), or by decreasing the content of basic amino acid residues (lysine residues, arginine residues and histidine residues), among the amino acid residues in the amino acid sequence of the polypeptide. In the invention, the pI of the specific polypeptide is a value measured by isoelectric focusing according to an ordinary method.

From the viewpoint of antigenicity of the specific polypeptide, each of a serine residue(s) and/or threonine residue(s) is preferably substituted by other amino acid residue. An example of the other amino acid residue for substitution of a serine residue or threonine residue is a lysine residue. For example, use of a lysine residue instead of a serine residue or threonine residue leads to introduction of an amino group to the specific polypeptide, which then results in an increased number of cross-linking points. As a result, the polypeptide tends to be more stable and less likely to be decomposed, achieving better properties for formulation.

The specific polypeptide is preferably a recombinant polypeptide from the viewpoints of reduction of antigenicity, mass production, safety, and the like. In the present description, the "recombinant peptide" means a polypeptide artificially prepared by a gene recombinant technology using *E. coli*, yeast, cultured cells, or the like as a host.

The solubility of the specific polypeptide in water is preferably not less than 2% by mass from the viewpoint of properties for formulation. The solubility in water in the invention means the solubility in water under normal pressure at 25° C.

From the viewpoint of the capacity to promote matrix production in cartilage cells, examples of the specific polypeptide include the following:

(1) a polypeptide having an amino acid sequence in which the number of RGD sequences contained per molecular weight of 10 kDa is not less than 0.30; the number of GFPGER (SEQ ID NO:12) sequences contained per molecular weight of 10 kDa is not less than 0.15; and the number of GVMGFP (SEQ ID NO:13) sequences contained per molecular weight of 10 kDa is less than 0.30; which polypeptide has a molecular weight of from 30 kDa to 80 kDa, and a pI of from 5.0 to 10.0;

(2) a polypeptide having an amino acid sequence composed of from 300 to 1400 amino acid residues in which the number of RGD sequences contained per molecular weight of 10 kDa is not less than 0.30; the number of GFPGER (SEQ ID NO:12) sequences contained per molecular weight of 10 kDa is not less than 0.15; and the number of GVMGFP (SEQ ID NO:13) sequences contained per molecular weight of 10 kDa is less than 0.30; which polypeptide has a pI of from 5.0 to 10.0;

(3) a polypeptide having an amino acid sequence in which the number of RGD sequences contained per molecular weight of 10 kDa is not less than 0.30; the number of GFPGER (SEQ ID NO:12) sequences contained per molecular weight of 10 kDa is not less than 0.15; and no GVMGFP (SEQ ID NO:13) sequence is contained; which polypeptide has a molecular weight of from 30 kDa to 80 kDa, and a pI of from 5.0 to 10.0;

(4) a polypeptide having an amino acid sequence in which the number of RGD sequences contained per molecular weight of 10 kDa is not less than 0.35; the number of GFPGER (SEQ ID NO:12) sequences contained per molecular weight of 10 kDa is not less than 0.20; and the number of GVMGFP (SEQ ID NO:13) sequences contained per molecular weight of 10 kDa is less than 0.30; which polypeptide has a molecular weight of from 40 kDa to 70 kDa, and a pI of from 5.0 to 10.0; and (5) a polypeptide having an amino acid sequence composed of from 300 to 1400 amino acid residues in which the number of RGD sequences contained per molecular weight of 10 kDa is not less than 0.35; the number of GFPGER (SEQ ID NO:12)sequences contained per molecular weight of 10 kDa is not less than 0.20; and the number of GVMGFP (SEQ ID NO:13) sequences contained per molecular weight of 10 kDa is less than 0.30; which polypeptide has a pI of from 5.0 to 10.0.

The specific polypeptide in the invention is preferably the polypeptide of SEQ ID NO: 1, 2 or 3 shown below, because of their high capacity to promote GAG production. In each sequence, RGD, GFPGER (SEQ ID NO:12), and GVMGFP (SEQ ID NO:13) sequences are indicated in bold. In SEQ ID NOs:1 to 3, each base corresponding to a serine residue or threonine residue in the amino acid sequence of natural form of human type II collagen is substituted by a glycine residue, alanine residue, lysine residue, or the like.

TABLE 2

| sequence | Number of residues | SEQ ID No. |
|---|---|---|
| GPQGARGQPGVMGFPGPKGANGEPGKAGEKGLPGAPGLRGLPGKDGEAGAAGPPGPAGPAGERGEQ<br>GAPGPPGFQGLPGPPGPPGEGGKPGDQGVPGEAGAPGLVGPRGERGFPGERGAPGAQGLQGPRGLP<br>GAPGPDGPKGAAGPAGPPGAQGPPGLQGMPGERGAAGIAGPKGDRGDVGEKGPEGAPGKDGGRGLGG<br>PIGPPGPAGANGEKGEVGPPGPAGAAGARGAPGERGEAGPPGPAGPAGPPGADGQPGAKGEQGEAGQ<br>KGDAGAPGPQGPGGAPGPQGPAGVAGPKGARGAQGPPGAAGFPGAAGRVGPPGLQGNPGPPGPPGPA<br>GKDGPKGARGDAGPPGRAGEPGLQGPAGPPGEKGEPGDDGPPGAEGPPGPQGLAGQRGIVGLPGQRG<br>ERGFPGLPGPAGEPGKQGAPGAAGDRGPPGPVGPPGLAGPAGEPGREGGPGADGPPGRDGAAGVKGD<br>RGEAGAVGAPGAPGPPGAPGPAGPPGPQGDRGEAGAQGP | 506 | 1 |
| GPQGARGQPGVMGFPGPKGANGEPGKAGEKGLPGAPGLRGLPGKDGEAGAAGPPGPAGPAGERGEQ<br>GAPGPPGFQGLPGPPGPPGEGGKPGDQGVPGEAGAPGLVGPRGERGFPGERGKPGAQGLQGPRGLP<br>GAPGKDGPKGAAGPAGPPGAQGPPGLQGMPGERGAAGIAGPKGDRGDVGEKGPEGAPGKDGGRGLGG<br>PIGPPGPAGANGEKGEVGPPGPAGAAGARGAPGERGEKGPPGPAGFAGPPGADGQPGAKGEQGEAGQ<br>KGDAGAPGPQGPKGAPGPQGPAGVAGPKGARGAQGPPGAAGFPGAAGRVGPPGLQGNPGPPGPPGPA<br>GKDGPKGARGDAGPPGRAGEPGLQGPAGPPGEKGEPGDDGPPGAEGPPGPQGLAGQRGIVGLPGQRG<br>ERGFPGLPGPKGEPGKQGAPGAKGDRGPPGPVGPPGLAGPAGEPGREGGPGADGPPGRDGAAGVKGD<br>RGEKGAVGAPGAPGPPGAPGPAGPPGPQGDRGEAGAQGP | 506 | 2 |
| MGFPGPKGANGEPGKAGEKGLPGAPGLRGLPGKDGEAGAAGPPGPAGPAGERGEQGAPGPPGFQGLP<br>GPPGPPGEGGKPGDQGVPGEAGAPGLVGPRGERGFPGERGKPGAQGLQGPRGLPGAPGKDGPKGAA<br>GPAGPPGAQGPPGLQGMPGERGAAGIAGPKGDRGDVGEKGPEGAPGKDGGRGLGGPIGPPGPAGANG<br>EKGEVGPPGPAGAAGARGAPGERGEKGPPGPAGFAGPPGADGQPGAKGEQGEAGQKGDAGAPGPQGP<br>KGAPGPQGPAGVAGPKGARGAQGPPGAAGFPGAAGRVGPPGLQGNPGPPGPPGPAGKDGPKGARGDA<br>GPPGRAGEPGLQGPAGPPGEKGEPGDDGPPGAEGPPGPQGLAGQRGIVGLPGQRGERGFPGLPGPKG<br>EPGKQGAPGAKGDRGPPGPVGPPGLAGPAGEPGREGGPGADGPPGRDGAAGVKGDRGEKGAVGAPKA<br>PGPPGAPGPAGPPGPQGDRGEAGAQGPMGFPGPKGANGEPGKAGEKGLPGAPGLRGLPGKDGEAGAA<br>GPPGPAGPAGERGEQGAPGPPGFQGLPGPPGPPGEGGKPGDQGVPGEAGAPGLVGPRGERGFPGER<br>GKPGAQGLQGPRGLPGAPGKDGPKGAAGPAGPPGAQGPPGLQG | 644 | 3 |

The polypeptide of the invention is preferably (A) a polypeptide having the amino acid sequence of SEQ ID NO:1, 2, or 3; (B) a polypeptide having the same amino acid sequence as the amino acid sequence of SEQ ID NO:1, 2, or 3 except that one or several amino acids are deleted, substituted and/or added, which polypeptide has a capacity to promote GAG production; or (C) a polypeptide having an amino acid sequence with a sequence identity of not less than 80% to the amino acid sequence of SEQ ID NO:1, 2, or 3, which polypeptide has a capacity to promote GAG production. The polypeptide of (C) is more preferably a polypeptide having an amino acid sequence with a sequence identity of not less than 90% to the amino acid sequence of SEQ ID NO:1, 2, or 3, which polypeptide has a capacity to promote GAG production; still more preferably a polypeptide having an amino acid sequence with a sequence identity of not less than 95% to the amino acid sequence of SEQ ID NO:1, 2, or 3, which polypeptide has a capacity to promote GAG production.

Further, the polypeptide of the invention is preferably (A1) a polypeptide composed of the amino acid sequence of SEQ ID NO:1, 2, or 3; (B1) a polypeptide composed of the same amino acid sequence as the amino acid sequence of SEQ ID NO:1, 2, or 3 except that one or several amino acids are deleted, substituted and/or added, which polypeptide has a capacity to promote GAG production; or (C1) a polypeptide composed of an amino acid sequence with a sequence identity of not less than 80% to the amino acid sequence of SEQ ID NO:1, 2, or 3, which polypeptide has a capacity to promote GAG production. The polypeptide of (C1) is more preferably a polypeptide composed of an amino acid sequence with a sequence identity of not less than 90% to the amino acid sequence of SEQ ID NO:1, 2, or 3, which polypeptide has a capacity to promote GAG production; still more preferably a polypeptide composed of an amino acid sequence with a sequence identity of not less than 95% to the amino acid sequence of SEQ ID NO:1, 2, or 3, which polypeptide has a capacity to promote GAG production.

In the amino acid sequence of each of the polypeptide of (B) and the polypeptide of (B1), 1 or several amino acid residues may be deleted, substituted and/or added. Although the number of the amino acid residues to be deleted, substituted and/or added varies depending on the total number of amino acid residues in the particular polypeptide, the number may be from 2 to 15, preferably from 2 to 5.

The specific polypeptide can be produced by a gene recombinant technology known to those skilled in the art. Examples of the method which may be used for producing the polypeptide include the methods described in EP 0926543 A1, EP 1014176 A2, U.S. Pat. No. 6,992,172, WO 01/34646, WO 2004/85473, and WO 2008/103041. More specifically, a gene encoding the amino acid sequence of the polypeptide of interest is obtained, and the gene is then incorporated into an expression vector to prepare a recombinant expression vector. The prepared recombinant expression vector is introduced into an appropriate host to prepare a transformant. By culturing the obtained transformant in an appropriate medium, the polypeptide of interest is produced. By recovering the produced polypeptide from the culture, the particular polypeptide according to the invention can be obtained.

The capacity to promote GAG production can be evaluated by bringing the polypeptide into contact with cartilage cells, and then measuring the GAG production after a predetermined period of time.

Specific examples of the evaluation method include the following method.

The subject polypeptide is dissolved in water for injection (for dissolving polypeptide) such that the polypeptide is contained in a predetermined amount, for example, 0 µg/ml, 0.2 µg/ml, or 20 µg/ml, to prepare sample liquids. To each well of a 24-well plate (24 WELL NON-TRATED PLATE, BD Company), 625 µl of each of the obtained sample liquids is placed. The samples are fixed in the wells by air-drying at 25° C. to provide a test plate.

To the test plate, cartilage cells derived from Japanese white rabbits are seeded at 20,000 cells/well, and culture is performed at 37° C. under 5% (v/v) $CO_2$. The culture supernatant is collected at Hour 2, Day 1, Day 2, Day 3, and Day 7 for quantification of GAG in the culture supernatant.

The quantification of GAG is carried out using a "SULFATED GLYCOSAMINOGLYCAN QUANTIFICATION KIT" (trade name, Seikagaku Biobusiness Corporation).

In the quantification, the medium in the wells of the test plate is discarded, and washing is carried out once using 1 ml/well of phosphate buffered saline (PBS). To each well after washing, 150 µl of the protease liquid included the kit is added, and the liquid is then stirred using a plate shaker. Thereafter, treatment is carried out at 50° C. for 2 hours, and then at 100° C. for 10 minutes. To 50 µl of each sample, 50 µl of the reaction buffer II included in the kit is added, and the resulting mixture is mixed, followed by addition of 150 µl of a DMMB (dimethylmethylene blue) dye solution thereto. The same operations are carried out for GAG standard solutions. After 5 minutes of the reaction, the absorbance is measured at a wavelength of 530 nm using a plate reader to perform quantification of GAG. The same operations are carried out for natural form of type II collagen. The amount of GAG in the case in which the subject polypeptide was used is compared with the amount of GAG in the case in which natural form of type II collagen was used, and, when the amount of GAG in the case in which the subject polypeptide was used is larger than the amount of GAG in the case in which natural form of type II collagen was used, the subject polypeptide is evaluated as having a capacity to promote GAG production. The quantification of GAG can also be carried out using a product equivalent to the above quantification kit, and examples of the equivalent product include the BLYSCAN GLYCOSAMINOGLYCAN ASSAY KIT (120 assays) (trade name, Biocolor Ltd., B1000).

[Scaffold Composition]

The scaffold composition according to the invention contains the specific polypeptide described above. As described above, the specific polypeptide contained in the scaffold composition can promote production of the matrix by cartilage cells when the polypeptide is brought into contact with the cartilage cells. Thus, the scaffold composition can promote the matrix production by cartilage cells.

The scaffold composition may contain, in addition to the specific polypeptide, one or more of other factors and the like that are known to promote the matrix production. Examples of such other factors include basic fibroblast growth factor (bFGF), parathyroid hormone, transforming growth factor β (TGFβ), insulin-like growth factor I (IGF-I), and insulin-like growth factor II (IGF-II). These other factors may be used singly, or in combination of two or more kinds thereof.

[Composition for Promoting GAG Production]

The composition for promoting GAG production according to the invention comprises the specific polypeptide described above. As described above, the specific polypeptide can promote production of GAG by cells when the polypeptide is brought into contact with the cells. Thus, the specific polypeptide can be preferably employed as a composition for promoting GAG production for uses in which promotion of GAG production is demanded.

Examples of the cells whose production of GAG is promoted by the composition for promoting GAG production according to the invention include cartilage cells, vascular endothelial cells, and corneal endothelial cells. The composition for promoting GAG production is particularly preferably used for cartilage cells.

The composition for promoting GAG production may contain, in addition to the specific polypeptide, one or more of other factors and the like that are known to promote the matrix production. Examples of such other factors include bFGF, parathyroid hormone, TGFµ, IGF-I, and IGF-II. These other factors may be used singly, or in combination of two or more kinds thereof

[Composition for Cartilage Tissue Restoration and Composition for Cartilage Cell Culture]

As described above, the specific polypeptide, scaffold composition, and composition for promoting GAG production according to the invention promote production of a specific matrix by cells when the polypeptide or composition is brought into contact with the cells. Thus, the polypeptide and compositions can be applied to various uses. Examples of such uses include restoration or regeneration of damaged tissue, for example, damaged cartilage.

That is, the invention also includes a composition for cartilage tissue restoration and a composition for cartilage cell culture, containing the specific polypeptide. Examples of the cartilage in such a case include articular cartilage (in the knee, shoulder or hip joint), vertebral cartilage, auricular cartilage, and nasal septal cartilage. The composition for cartilage tissue restoration and the composition for cartilage cell culture, containing the specific polypeptide are particularly preferably used as compositions for restoration or regeneration of damaged cartilage in joints. Such use allows proliferation of cartilage cells and/or favorable repair of a cartilage tissue. The invention also includes a method for restoration or regeneration of damaged cartilage, comprising administering the composition for cartilage tissue restoration to the damaged area of cartilage.

[Other Uses]

The invention also includes uses of the specific matrix-producing polypeptide for production of a scaffold composition, composition for cartilage tissue restoration, composition for cartilage cell culture, or composition for promoting glycosaminoglycan production.

Further, the GAG production-promoting polypeptide, scaffold composition, and/or composition for promoting GAG production can be used for analyzing functions or properties of cells having a GAG production capacity, for example, cartilage cells, or for carrying out a test or study utilizing the functions or properties of these cells.

EXAMPLES

The invention is described in detail by way of Examples. However, the invention is not limited to the Examples.

Examples 1 to 3

In order to produce GAG production-promoting polypeptides RCP #4 to RCP #6, which have the amino acid sequences of SEQ ID NO:1 to SEQ ID NO:3, polynucleotides (SEQ ID NO:5 to SEQ ID NO:7) having base sequences corresponding to the amino acid sequences of SEQ ID NO:1 to SEQ ID NO:3 were synthesized by an ordinary method. The obtained polynucleotides were amplified by polymerase chain reaction (PCR), and each of the resulting amplification products was introduced into pPICZαA (Invitrogen), which is a plasmid containing the a-factor signal for protein secretion and the Zeocin resistance gene for selection, using an IN-FUSION HD CLONING KIT (Clontech Inc.).

*Pichia pastoris* cells were transformed with the obtained plasmid by electroporation, and transformed yeast strains were selected based on the resistance to an antibiotic Zeocin.

Polypeptides were produced based on the introduced polynucleotides according to the methods disclosed in EP-A-0926543, EP-A-1014176, and WO 01/34646.

More specifically, the yeast strains obtained as described above were grown using the YNB (Yeast Nitrogen Base w/o amino acids) medium (BD Corporation), and then cultured in 3-L jar fermenters (B.E. Marubishi Co., Ltd.). More specifically, each yeast strain was first grown in a medium containing glycerol as a carbon source, and, from 1 hour before completion of the addition of glycerol, methanol was added as a carbon source to perform culture. After 96 hours of the culture, the culture supernatant was collected, and SDS-PAGE was carried out using the collected culture supernatant in order to confirm expression of the polypeptide of interest.

Culture supernatants for which expression of the polypeptides of interest could be confirmed were subjected to purification with a cation-exchange chromatography CAPTO-S (trade name, GE Healthcare) and an anion-exchange chromatography CAPTO-Q: (trade name, GE Healthcare) using an AKTA EXPLORER (trade name, GE Healthcare), to obtain polypeptides of interest RCP #4 to RCP #6.

Properties of the polypeptides are show in Table 4. Each isoelectric point (pI) is a calculated value. The molecular weight was measured by ESI-MS (Q-TOF PREMIER, manufactured by Waters Corporation). The solubility of each polypeptide in water was not less than 2% by mass under normal pressure at 25° C.

In Table 4, "normal" as described for the amount of lysine means that each residue corresponding to a serine residue or threonine residue in the amino acid sequence of natural form of human type II collagen is substituted by a glycine residue or alanine residue, and "high" means that each residue corresponding to a serine residue or threonine residue in the amino acid sequence of natural form of human type II collagen is substituted by a lysine residue.

Each identity indicates the identity to the amino acid sequence of natural form of human type II collagen. The symbol "*" in Table 4 indicates that, in cases in which the polypeptide contained repeated sequences, the identity (%) was determined for the corresponding portions in the polypeptide sequence after exclusion of the repeated portion.

Comparative Examples 1 to 4

As polypeptides for comparison, polypeptides RCP #7 and RCP #2, R-II collagen, and natural form of human type II collagen were prepared (Comparative Examples 1 to 4).

As shown in Table 3 and Table 4, the polypeptide RCP #7 (SEQ ID NO:8) has an amino acid sequence in which not less than 0.3 GVMGFP (SEQ ID NO:13) sequences are contained per 10 kDa. As shown in Table 3 and 4, the polypeptide RCP #2 (SEQ ID NO:9) has an amino acid sequence containing no GFPGER (SEQ ID NO:12)sequence. Each of the R-II collagen and the natural form of human type II collagen (SEQ ID NO:4) contains an amino acid sequence in which not more than 0.15 GFPGER (SEQ ID NO:12) sequences are contained per 10 kDa.

The polypeptides RCP #7 and RCP #2 were obtained in the similar manner as in Examples 1 to 3 except that the corresponding polynucleotides (SEQ ID NOs:10 and 11) were used.

The R-II collagen was obtained in the similar manner as in Examples 1 to 3 except that a polynucleotide having a base sequence corresponding to the amino acid sequence of SEQ ID NO:4 was provided. The serine residues and threonine residues were not substituted by other amino acid residues, and the identity to natural form of human type II collagen was 100%.

Properties of the polypeptides are shown in Table 3 and Table 4. In Table 4, "R-II" indicates the R-II collagen. The symbol "*" in Table 4 indicates that, in cases in which the polypeptide contained repeated sequences, the identity (%) was determined for the corresponding portions in the polypeptide sequence after exclusion of the repeated portion. In Table 4, "Natural Form of type II collagen" means natural form of human type II collagen.

TABLE 3

| | sequence | Number of residues | SEQ ID No. |
|---|---|---|---|
| RCP#7 | GPQGARGQPGVMGFPGPKGANGEPGKAGEKGLPGAPGLRGLPGKDGEAGAAGPPGPAGPAGERGEQG APGPPGFQGLPGPPGPPGEGGKPGDQGVPGEAGAPGLVGPRGERGFPGERGLPGAQGLQGPRGLPGA PGKDGPKGAAGPAGPPGAQGPPGLQGMPGERGAAGIAGPKGDRGDVGEKGPEGAPGKDGGRGLGGPI GPPGPAGANGEKGEVGPPGPAGAAGARGAPGERGEKGPPGPAGFAGPPGADGQPGAKGEQGEAGQKG DAGAPGPQGPKGAPGPQGPAGVAGPKGARGAQGPPGAAGFPGAAGRVGPPGLQGNPGPPGPPGPAGK DGPKGARGDAGPPGRAGEPGLQGPAGPPGEKGEPGDDGPPGAEGPPGPQGLAGQRGIVGLPGQRGER GFPGLPGPKGEPGKQGAPGAKGDRGPPGPVGPPGLAGPAGEPGREGGPGADGPPGRDGAAGVKGDRG EKGAVGAPGAPGPPGAPGPAGPPGPQGDRGEAGAQGPGPQGARGQPGVMGFPGPKGANGEPGKAGEK GLPGAPGLRGLPGKDGEAGAAGPPGPAGPAGERGEQGAPGPPGFQGLPGPPGPPGEGGKPGDQGVPG EAGAPGLVGPRGERGFPGERGKPGAQGLQGPRGLPGAPGKDGPKGAAGPAGPPGAQGPPGLQG | 666 | 8 |
| RCP#2 | PGERGAAGIAGPKGDRGDVGEKGPEGAPGKDGGRGLGGPIGPPGPAGANGEKGEVGPPGPAGAAGAR GAPGERGEKGPPGPAGFAGPPGADGQPGAKGEQGEAGQKGDAGAPGPQGPKGAPGPQGPAGVAGPKG ARGAQGPPGAAGFPGAAGRVGPPGLQGNPGPPGPPGPAGKDGPKGARGDAGPPGRAGEPGLQGPAGP PGEKGEPGDDGPPGAEGPPGPQGKAGQRGIVGLPGQRGERGFPGLPGPKGEPGKQGAPGAKGDRGPP GPVGPPGLAGPAGEPGREGGPGADGPPGRDGAAGVKGDRGEKGAVGAPGAPGPPGAPGPAGPPGPQG DRGEAGAQGPPGERGAAGIAGPKGDRGDVGEKGPEGAPGKDGGRGLGGPIGPPGPAGANGEKGEVGP PGPAGAAGARGAPGERGEKGPPGPAGFAGPPGADGQPGAKGEQGEAGQKGDAGAPGPQGPKGAPGPQ GPAGVAGPKGARGAQGPPGAAGFPGAAGRVGPPGLQGNPGPPGPPGPAGKDGPKGARGDAGPPGRAG EPGLQGPAGPPGEKGEPGDDGPPGAEGPPGPQGLAGQRGIVGLPGQRGERGFPGLPGPKGEPGKQGA PGAKGDRGPPGPVGPPGLAGPAGEPGREGGPGADGPPGRDGAAGVKGDRGEKGAVGAPGAPGPPGAP GPAGPPGPQGDRGEAGAQGP | 690 | 9 |

<Evaluation>

The obtained polypeptides were evaluated as follows for their capacity to promote proliferation of cartilage cells, and their capacity to promote production of the extracellular matrix. Before the evaluation, test plates were prepared as follows.

(1) Preparation of Plates Coated with GAG Production-promoting Polypeptide

Each of the polypeptides RCP #4 to #6, corresponding to Examples of the invention; and RCP #7, RCP #2, R-II collagen and natural form of human type II collagen, corresponding to Comparative Examples of the invention; was dissolved in a solution for dissolving RCP #4 to #7 and #2, and R-II collagen (water for injection), or in a solution for dissolving natural form of human type II collagen (acidic solution prepared by adjusting the pH of distilled water to 3 with 1 M HCl) such that the polypeptide was contained at 0.2 µg/ml, 2 µg/ml, or 20 µg/ml, to prepare sample solutions. To each well of 24-well plates (24 well non-treated plate, BD Company), 625 µl of each of the obtained sample solutions was placed. The samples were fixed in the wells by air-drying at 25° C. to prepare test plates.

(2) Evaluation of Proliferation of Cartilage cells

For the evaluation of proliferation of cartilage cells, CHONDROCYTE CULTURE KIT (Code: CHC02) purchased from Primary Cell Co., Ltd. was used.

To the test plates prepared as described above, cartilage cells derived from Japanese white rabbits, included in the kit, were seeded at 20,000 cells/well, and culture was performed at 37° C. under 5% (v/v) $CO_2$. For the culture, the "differentiation medium" (RPMI1640, serum, ascorbic acid, etc.) included in the kit was used. Cartilage cells in each well were collected at Hour 2, Day 1, Day 2, Day 3, and Day 7 after the beginning of the culture, and the number of cartilage cells was quantified.

More specifically, the medium in the test plates was discarded, and washing was carried out once using 1 ml/well of PBS, followed by adding 150 µl of trypsin-EDTA to each well and leaving the plates to stand for 1 minute, thereby detaching the cells attached to the test plates. Into each well, 150 µl of the medium described above was added to prepare a cell suspension, and trypan blue was added thereto, followed by counting the number of live cells using a hemacytometer. The capacity to promote proliferation of cartilage cells was evaluated as follows based on the number of obtained live cells. The results are shown in Table 4. In Table 4, "-" in the column showing the evaluation of proliferation of cartilage cells means that the evaluation was not carried out.

S: The number of cells was more than 125% with respect to the number of cells obtained by the culture after addition of natural form of human type II collagen.

A: The number of cells was from more than 100% to 125% with respect to the number of cells obtained by the culture after addition of natural form of human type II collagen.

B: The number of cells was from more than 75% to 100% with respect to the number of cells obtained by the culture after addition of natural form of human type II collagen.

C: The number of cells was not more than 75% with respect to the number of cells obtained by the culture after addition of natural form of human type II collagen.

(3) Evaluation of Cartilage Matrix Production

In the similar manner as in the (2) described above, cartilage cells derived from Japanese white rabbits were cultured with each polypeptide in each test plate prepared in the (1) described above. GAG as a matrix was quantified at Hour 2, Day 1, Day 2, Day 3, and Day 7 after the beginning of the culture. The quantification of GAG was carried out using a "SULFATED GLYCOSAMINOGLYCAN QUANTIFICATION KIT" (Seikagaku Biobusiness Corporation).

More specifically, the medium in the wells of the test plates was discarded, and washing was carried out once using 1 ml/well of PBS, followed by adding 150 µl of the protease liquid included the kit to each well and stirring the liquid using a plate shaker. Subsequently, the reaction was allowed to proceed at 50° C. for 2 hours, and then at 100° C. for 10 minutes. To 50 µl of each sample, 50 µl of the reaction buffer II included in the kit was added, and the resulting mixture was mixed, followed by addition of 150 µl of a DMMB dye solution thereto. The same operations were carried out for the GAG standard solutions included in the kit. After 5 minutes of the reaction, the absorbance was measured at a wavelength of 530 nm using a plate reader (Sunrise (trade name) SUNRISE RAINBOW THERMO RC [model number], manufactured by TECAN Ltd.) to perform quantification of GAG. The results are shown in FIG. 1. The capacity to promote cartilage matrix production was evaluated as follows based on the amount of GAG. The results are shown in Table 4.

S: The amount of GAG produced was more than 125% with respect to the amount of GAG produced by the culture after addition of natural form of human type II collagen.

A: The amount of GAG produced was from more than 100% to 125% with respect to the amount of GAG produced by the culture after addition of natural form of human type II collagen.

B: The amount of GAG produced was from more than 75% to 100% with respect to the amount of GAG produced by the culture after addition of natural form of human type II collagen.

C: The amount of GAG produced was not more than 75% with respect to the amount of GAG produced by the culture after addition of natural form of human type II collagen

TABLE 4

| | Amount of lysine | pI | Number of amino acid residues | Molecular weight (kDa) | RGD(A) Number/ total length (sequences) | RGD(A) Number/ 10 kDa (sequences) | GFPGER(B) Number/ total length (sequences) | GFPGER(B) Number/ 10 kDa (sequences) | GVMGFP(C) Number/ total length (sequences) | GVMGFP(C) Number/ 10 kDa (sequences) | (A)/ [(B)+(C)] | Identity (%) | Matrix production | Cell proliferation | SEQ ID No. |
|---|---|---|---|---|---|---|---|---|---|---|---|---|---|---|---|
| RCP#4 | normal | 5.48 | 506 | 45.0 | 2.00 | 0.44 | 1.00 | 0.22 | 1.00 | 0.22 | 1.00 | 94.9 | S | A | 1 |
| RCP#5 | high | 9.14 | 506 | 45.3 | 2.00 | 0.44 | 1.00 | 0.22 | 1.00 | 0.22 | 1.00 | 94.9 | S | B | 2 |
| RCP#6 | high | 9.14 | 644 | 57.8 | 2.00 | 0.35 | 2.00 | 0.35 | 0.00 | 0.00 | 1.00 | 94.7* | S | B | 3 |

TABLE 4-continued

|  | Amount of lysine | pI | Number of amino acid residues | Molecular weight (kDa) | RGD(A) Number/ total length (sequences) | RGD(A) Number/ 10 kDa (sequences) | GFPGER(B) Number/ total length (sequences) | GFPGER(B) Number/ 10 kDa (sequences) | GVMGFP(C) Number/ total length (sequences) | GVMGFP(C) Number/ 10 kDa (sequences) | (A)/ [(B)+(C)] | Identity (%) | Matrix production | Cell proliferation | SEQ ID No. |
|---|---|---|---|---|---|---|---|---|---|---|---|---|---|---|---|
| RCP#7 | high | 9.34 | 666 | 59.8 | 2.00 | 0.33 | 2.00 | 0.33 | 2.00 | 0.33 | 0.50 | 94.9* | A | B | 8 |
| RCP#2 | high | 8.62 | 690 | 61.4 | 4.00 | 0.65 | 0 | 0.00 | 0.00 | 0.00 | — | 94.2* | A | B | 9 |
| R-II | — | 9.27 | 1014 | 90.5 | 3.00 | 033 | 1.00 | 0.11 | 1.00 | 0.11 | 1.50 | 100 | C | — | 4 |
| Natural form of type II collagen | — | 9.27 | 1014 | 90.5 | 3.00 | 0.33 | 1.00 | 0.11 | 1.00 | 0.11 | 1.50 | 100 | A | A | 4 |

As shown in Table 4 and FIG. 1, it was found that any of the polypeptides of the invention, RCP #4 to #6, promoted the GAG production significantly more efficiently than the natural form of human type II collagen. Moreover, any of the polypeptides of the invention, RCP #4 to #6, could promote the proliferation of cartilage cells equally to, or more efficiently than, the polypeptides of Comparative Examples 1 to 3.

Thus, the polypeptides RCP #4 to #6 were found to be scaffold compositions that are excellent in promotion of cartilage matrix production as well as in promotion of proliferation of cartilage cells.

It was also found that the cell proliferation capacity further increases when the pI is not more than 6.0 (see the result on RCP #4).

It was also found that, since the polypeptides RCP #4 to #6 were excellent in production of glycosaminoglycan and allowed proliferation of cartilage cells, these polypeptides can be used as compositions for cartilage tissue restoration, composition for cartilage cell culture, or composition for promoting glycosaminoglycan production Thus, the invention can provide a scaffold composition excellent in promotion of extracellular-matrix production by cartilage cells, a composition for cartilage tissue restoration, a composition for promoting glycosaminoglycan production, and a composition for cartilage cell culture, and a material therefor.

The disclosure of Japanese Patent Application No. 2012-213110, filed on Sep. 26, 2012, is hereby incorporated by reference in its entirety.

All the literatures, patent applications and technical standards described in the present description are hereby incorporated by reference to the same extent as in cases in which each literature, patent application or technical standard is concretely and individually described to be incorporated by reference.

The invention claimed is:

1. polypeptide which is
   (1) a polypeptide consisting of the amino acid sequence of SEQ ID NO: 1;
   (2) a polypeptide consisting of the amino acid sequence of SEQ ID NO: 1, except that 1 to 15 amino acids are deleted, substituted and/or added, wherein said polypeptide has a capacity to promote glycosaminoglycan production;
   (3) a polypeptide consisting of the amino acid sequence of SEQ ID NO: 2;
   (4) a polypeptide consisting of the amino acid sequence of SEQ ID NO: 2, except that 1 to 15 amino acids are deleted, substituted and/or added, wherein said polypeptide has a capacity to promote glycosaminoglycan production;
   (5) a polypeptide consisting of the amino acid sequence of SEQ ID NO: 3; or
   (6) a polypeptide consisting of the amino acid sequence of SEQ ID NO: 3, except that 1 to 15 amino acids are deleted, substituted and/or added, wherein said polypeptide has a capacity to promote glycosaminoglycan production;
   wherein in the polypeptides of (1)-(6), the number of RGD sequences contained per molecular weight of 10 kDa is not less than 0.30, the number of GFPGER sequences contained per molecular weight of 10 kDa is not less than 0.15, and the number of GVMGFP sequences contained per molecular weight of 10 kDa is less than 0.30.

2. A scaffold composition comprising the polypeptide according to claim 1.

3. A composition for cartilage tissue restoration, comprising the polypeptide according to claim 1.

4. A composition for cartilage cell culture, comprising the polypeptide according to claim 1.

5. A composition for promoting glycosaminoglycan production, comprising the polypeptide according to claim 1.

6. A method for regeneration or restoration of cartilage comprising administering to a damage area of the cartilage the polypeptide according to claim 1.

7. A method for performing a cartilage cell culture comprising administering to said culture the polypeptide according to claim 1.

8. A method for promoting a cellular production of glycosaminoglycans in an extracellular matrix comprising administering to said matrix the polypeptide according to claim 1.

9. The polypeptide according to claim 1, having an isoelectric point (pI) of not more than 6.0.

10. The polypeptide according to claim 1, wherein the solubility of the polypeptide in water is at least 2% by mass.

11. The polypeptide according to claim 1, which consists of the amino acid sequence of SEQ ID NO:1, 2, or 3 except that 1 to 5 amino acids are deleted, substituted and/or added, wherein said polypeptide has a capacity to promote glycosaminoglycan production.

12. The polypeptide according to claim 1, which consists of the amino acid sequence of SEQ ID NO:1, 2, or 3.

* * * * *